United States Patent [19]

Caskey et al.

[11] Patent Number: 5,552,282
[45] Date of Patent: Sep. 3, 1996

[54] DIAGNOSIS OF MYOTONIC MUSCULAR DYSTROPHY

[75] Inventors: C. Thomas Caskey, West University, Tex.; Ying-Hui Fu, Columbus, Ohio; David L. Friedman, Houston, Tex.; Antonio Pizzuti, Milan, Italy; Raymond G. Fenwick, Sugarland, Tex.

[73] Assignee: Baylor College of Medicine, Houston, Tex.

[21] Appl. No.: 484,044

[22] Filed: Jun. 6, 1993

Related U.S. Application Data

[63] Continuation of Ser. No. 019,940, Feb. 19, 1993, abandoned.

[51] Int. Cl.$^6$ .............................. C12Q 1/68; C12P 19/34; C07H 21/04; C12N 15/00
[52] U.S. Cl. ........................... 435/6; 435/91.1; 435/91.2; 435/91.21; 536/24.31; 536/23.5; 536/24.33; 536/25.3; 935/1; 935/4; 935/8; 935/76; 935/77; 935/78
[58] Field of Search .............................. 435/6, 91.1, 91.2, 435/91.21; 536/24.31, 23.5, 24.33, 25.3; 935/1, 4, 8, 76, 77, 78

[56] References Cited

PUBLICATIONS

Rick Weiss, "Dazzled by Tortured Data", *Washington Post Health*, Nov. 23, 1993, p. 6.
Bartlett et al., *Science*, vol. 235, pp. 1648–1650, Mar. 27, 1987.
Sambrook et al., *Molecular Cloning A Laboratory Manual*, 2nd Ed., Cold Spring Harbor Laboratory Press, 5, 2–3.58, 1989.
Burke et al., *Science*, vol. 236, 806–812, 15 May 1987.
MiLunsky et al., *American J. Obstet. Gynecol.*, vol. 164, No. 3, 751–755, Mar. 1991.

*Primary Examiner*—W. Gary Jones
*Assistant Examiner*—Bradley L. Sisson
*Attorney, Agent, or Firm*—Fulbright & Jaworski L.L.P.

[57] ABSTRACT

The present invention includes a DNA clone from the myotonic muscular dystrophy gene, a cosmid probe to the myotonic dystrophy site, as well as methods of detecting myotonic muscular dystrophy using RFLP. The method involves the steps of digesting DNA from an individual to be tested with a restriction endonuclease and detecting the restriction fragment length polymorphism with hybridization to probes within the myotonic muscular locus and southern blot analysis. Alternatively, the myotonic muscular dystrophy gene can be measured by determining the amount of mRNA or measuring the amount of protein with an antibody. Further, the myotonic muscular dystrophy gene defect can be detected using either fluorescence in situ hybridization or pulsed field gel electrophoresis using the probes described herein.

17 Claims, 15 Drawing Sheets

1   cgcccctagcggtcggggaggagggccgggtccgcggccgaacgggctcgaag
61  ggtccttgtagccggaatGCTGCTGCTGCTGCTgggggat
121 cacagaccattcctttcggccaggctgaggcctgacgtgatgggcaaactgcag

Figure 1

| AAA | AGA | CAA | GAA | GGA | TAA | TGA |
| AAC | AGC | CAC | GAC | GGC | TAC | TGC |
| AAG | AGG | CAG | GAG | GGG | TAG | TGG |
| AAT | AGT | CAT | GAT | GGT | TAT | TGT |
| ACA | ATA | CCA | GCA | GTA | TCA | TTA |
| ACC | ATC | CCC | GCC | GTC | TCC | TTC |
| ACG | ATG | CCG | GCG | GTG | TCG | TTG |
| ACT | ATT | CCT | GCT | GTT | TCT | TTT |

CACCAC
CGGCGG
GCTGCT
TCCTCC
TCGTCG

Figure 7

DIAGNOSIS OF MYOTONIC MUSCULAR DYSTROPHY

This application is a continuation of application Ser. No. 08/019,940, filed Feb. 19, 1993, abandoned.

FIELD OF THE INVENTION

This invention relates to the field of molecular diagnosis of myotonic muscular dystrophy.

BACKGROUND

The myotonic muscular dystrophy (DM) disease is the most common adult muscular dystrophy in man with a prevalence of 1 in 10,000. The disorder is inherited in an autosomal dominant manner with variable expression of symptoms from individual to individual within a given family. Furthermore, the phenomenon of anticipation (increasing disease severity over generations) is well documented for DM. This is particularly evident when an affected mother transmits the gene for the disease to her offspring. These offspring have a high incidence of mental retardation and profound infantile myotonia. Adult patients with DM manifest a pleiotropic set of symptoms including myotonia, cardiac arrhythmias, cataracts, frontal baldness, hypogonadism, and other endocrine dysfunctions. There is no evidence that myotonic muscular dystrophy may be caused by defects in more than one gene.

A myotonic muscular dystrophy gene has been mapped to human chromosome position 19q13.3. Both a genetic and physical map of the region was developed by a group of investigators acting as a voluntary consortium under sponsorship of the Muscular Dystrophy Association. The genetic linkage studies identified two RFLP alleles, D10 and X75, which are polymerase chain reaction (PCR)-based dinucleotide polymorphisms and are tightly linked to DM.

Two disorders, Kennedy disease and fragile X syndrome, are associated with triplet nucleotide amplification. The triplet is CAG in the Kennedy disease gene and CGG in the fragile X syndrome gene. Repeat lengths in Kennedy disease have been reported as 40–57 units, whereas the normal range is 11–31 repeats. In the case of fragile X syndrome, the CGG repeat sequence becomes unstable once greater than 52 units long and is predisposed to amplification during female meiosis. The molecular basis of the Sherman paradox has now been explained for fragile X syndrome. The generation-to-generation progressive amplification of the CGG triplet repeat in fragile X syndrome correlates with increasing disease severity and lack of expression of the FMR-1 gene.

The present application provides a new method of sequence scanning for triplet repeats which are GC-rich and thus suspect for genetic instability by amplification/deletion/translocation. This method successfully identified a putative protein kinase gene in patients with DM. This application also provides rapid and simple methods for accurate means of DM diagnosis. The gene, myotonin protein kinase, was discovered by molecular cloning, predicted to be a protein kinase on the basis of sequence motif homology, characterized with regard to its sequence and alternative spliced forms, and found to be altered in expression in tissues of patients with DM.

SUMMARY OF THE INVENTION

An object of the present invention is a method for cloning human disease genes with GC-rich oligonucleotides screening method.

An object of the present invention is a method for diagnosing myotonic muscular dystrophy.

A further object of the present invention is a provision of a sequence of the DM gene.

Another object of the present invention is a method of detecting the myotonic muscular dystrophy desease by measuring GCT repeats.

An additional object of the present invention is a method of detecting the myotonic muscular dystrophy disease by measuring the mRNA or protein from the DM gene.

A further object of the present invention is a vector for expression of myotonic protein kinase.

Another object of the present invention is the provision of antibodies to myotonic protein kinase.

An additional object of the present invention is a diagnostic test for myotonic muscular dystrophy.

Thus in accomplishing the foregoing objects there is provided in accordance with one aspect of the present invention as a composition of matter, a 3.2 kb cDNA clone containing the DM gene. A further aspect is a 11613 bp genomic DNA sequence (SEQ ID NO. 10) containing the DM gene.

A further embodiment of the present invention is a method of detecting DM comprising the steps of digesting DNA from an individual to be tested with a restriction endonuclease and detecting the restriction fragment length polymorphism by hybridization to probes within the DM locus and southern blot analysis. In a preferred embodiment of the present invention, the probe is pMDY1 and the restriction endonucleases are selected from the group consisting of Nco1, Ban1, and Taq1.

Alternate embodiments of the present invention include detecting DM by measuring the expression of the DM gene either as the amount of mRNA expressed or as the amount of DM protein produced. Another embodiment of the present invention includes a method of detecting DM comprising the steps of detecting variation in the (CTG)n repeat at the 3' end of the DM gene by measuring the length of the repeat, wherein n for normal ranges between 5 to 33 and n for DM is greater than 35. A variety of methods are available to detect the dosage measurements of the repeat. These procedures can be selected from the group consisting of visual examination, densitometry measurement, quantitative radioactivity, and quantitative fluorescence as well as pulsed field gel electrophoresis and fluorescence in situ hybridization.

Other and further objects, features and advantages will be apparent and eventually more readily understood from a reading of the following specification and by reference to the accompanying drawings forming a part thereof, wherein examples of the present preferred embodiments of the invention are given for the purpose of the disclosure.

DESCRIPTION OF THE DRAWINGS

FIG. 1 is a sequence of the GCT triplet repeat (upper case) and its flanking regions (lower case). The locations of PCR primers are shown by solid lines with arrows. The complete 1.4 kb sequence (PMDY1) is in SEQ. ID. No. 1.

FIG. 7 shows the triplet repeat sequences.

Figure 2:
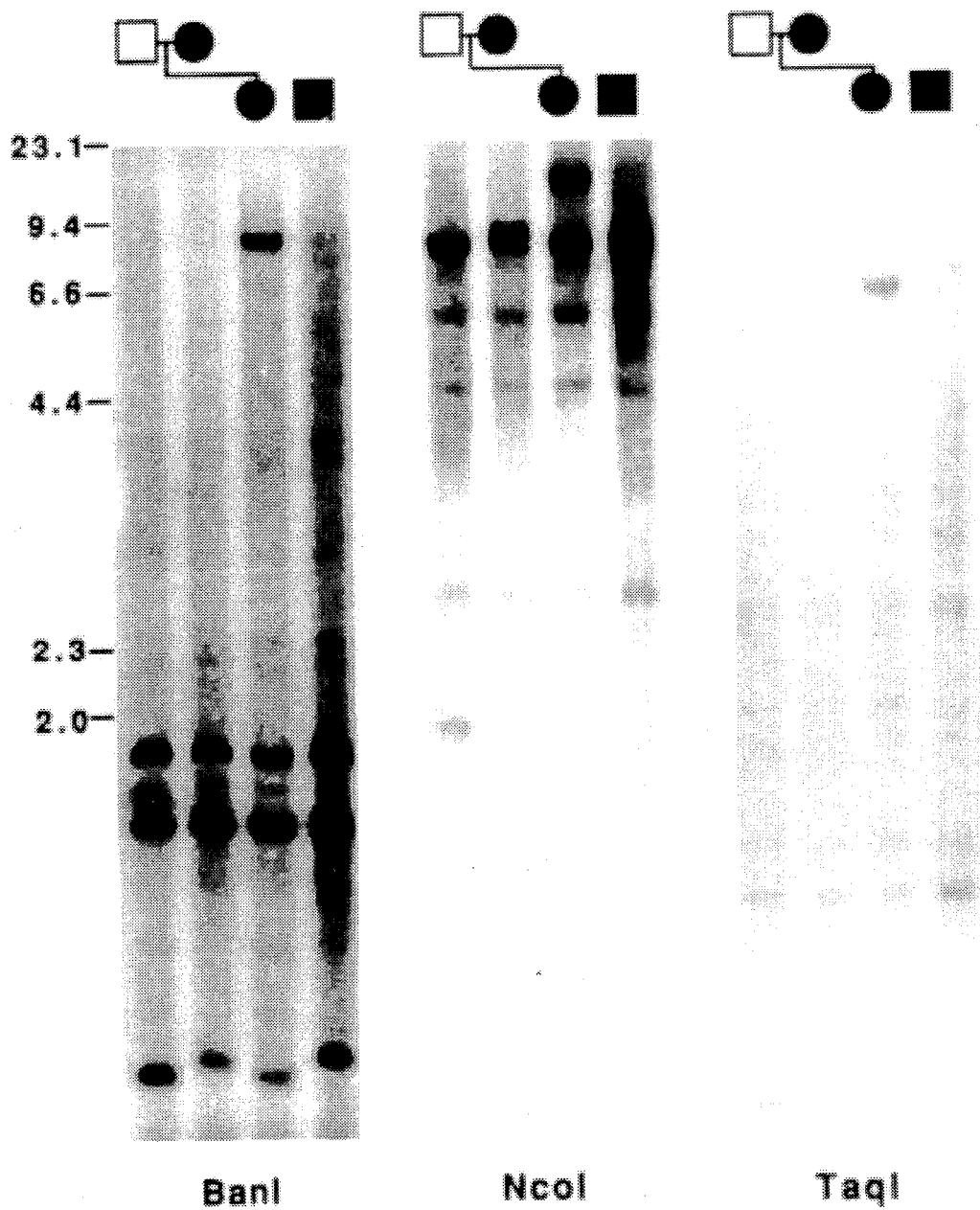
FIG. 2 shows Southern analysis of leukocyte DNA with probes containing the GCT repeat from pMDY1 and demonstrates that sequence expansion is the molecular alteration associated with myotonic dystrophy.

The drawings and figures are not necessarily to scale and certain features mentioned may be exaggerated in scale as shown in schematic form in the interest of clarity and conciseness.

DETAILED DESCRIPTION OF THE INVENTION

It will be readily apparent to one skilled in the art that variations, substitutions and modifications may be made to the invention disclosed herein without departing from the scope and the spirit of the invention.

Each sample to be tested herein for the DM mutation site is derived from genomic DNA, mRNA or protein. The source of the genomic DNA to be tested can be any medical specimen which contains DNA. Some examples of medical specimens include blood, semen, vaginal swabs, buccal mouthwash, tissue, hair, skin, amniotic fluid and mixture of body fluids.

As used herein the term "polymerase chain reaction" or "PCR" refers to the PCR procedure described in the patents to Mullis, et al., U.S. Pat. Nos. 4,683,195 and 4,683,202. The procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5)separating said extension products from said templates to produce single-stranded molecules; and (6) amplifying said single-stranded molecules by repeating at least once said annealing, extending and separating steps.

As used herein fluorescence in situ hybridization or "FISH" refers to the procedure described in Wotta, et al., Am. J. of Human Genetics, 46, 95–106 (1988) and Kievits, et al., Cytogenet. Cell Genet., 53134-136 (1990). The procedure basically involves the steps of preparing interphase or metaphase spreads from cells of peripheral blood lymphocytes and hybridizing labeled probes to the interphase or metaphase spreads. Using probes with mixed labels allows visualization of space, order and distance between hybridization sites. After hybridization the labels are examined to determine the order and distance between the hybridization sites.

As used herein, the term "pulsed field gel electrophoresis" or "PFGE" refers to a procedure described by Schwartz, et al., Cold Springs Harbor Symposium, Quantitative Biology, 47:189–195 (1982). The procedure basically comprises running a standard electrophoresis gel (agarose, polyacrylamide or other gel known to those skilled in the art) under pulsing conditions. One skilled in the art recognizes that the strength of the field as well the direction of the field is pulsed and rotated in order to separate megabase DNA molecules. Current commercial systems are computer controlled and select the strength, direction and time of pulse depending on the molecular weight of DNA to be separated.

The following examples are offered by way of illustration and are not intended to limit the invention in any manner. In the examples all percentages are by weight for solids and by volume for liquids and all temperatures are in degrees celsius unless otherwise noted.

EXAMPLE 1

Isolation and Identification of DM Locus

Yeast artificial chromosomes (YACs) isolated from the St. Louis library which span the DM locus were used. YAC clones 231G8 and 483E7 were subcloned into cosmids and human clones were identified by the presence of common repeat sequences.

YACs 231G8 and 483E7 DNA were partially digested by Sau3A and cloned into cosmid vector "Super Cos" (Stratagene). Human clones were identified by their hybridization with radiolabeled total human DNA, selected and arrayed on a gridded plate. Duplicate filter lifts were screened for clonal specific triplet repeats by their hybridization to a mixture of 4 radiolabeled oligonucleotides. Two positive cosmids (MDY1 and MDY2) were identified on the grid. These 2 cosmids were then found to contain sequences in common including BamHI fragments of 1.4 and 1.35 kb. The 1.4 kb BamHI fragment was then identified to contain the triplet repeat sequence.

Using hybridization techniques, a mixture of 4 oligonucleotides consisting of tandemly repeated GC-rich trinucleotides (CAC, GCT, TCC, TCG) identified 2 out of 300 cosmids (cosmids MDY1 and MDY2). This set of 4 triplet repeats (each 21 nucleotides in length) include 24 of 60 possible triplet repeats with emphasis on the GC-rich ones. The CGG repeat was examined separately. The 2 positive cosmids were found to be overlapping with each other. A 1.4 kb BamHI fragment which specifically hybridized to the GCT repeat was identified and subcloned into pBluescript (pMDY1). The sequence of pMDY1 was determined by means of the dideoxynucleotide termination method and an ABI 373 automated fluorescent DNA sequencer (FIG. 1). Sequence of the pMDY1 was determined by using a combination of dideoxynucleotide termination reaction and the Taq DyeDeoxy™ terminator cycle sequencing reaction (Applied Biosystems). The sequencing reactions were analyzed on an automated DNA sequencer (ABI 373). As predicted by the oligonucleotide hybridization, a region containing 11 repeats of the GCT triplet was identified. This triplet is known to be highly polymorphic and unstable in the androgen receptor gene. Thus, a mixed oligonucleotide probe has successfully identified a short (1.4 kb) candidate sequence for genetic instability from 2 YACs at the DM locus.

EXAMPLE 2

Genetic Instability of DM Locus

Figure 3:
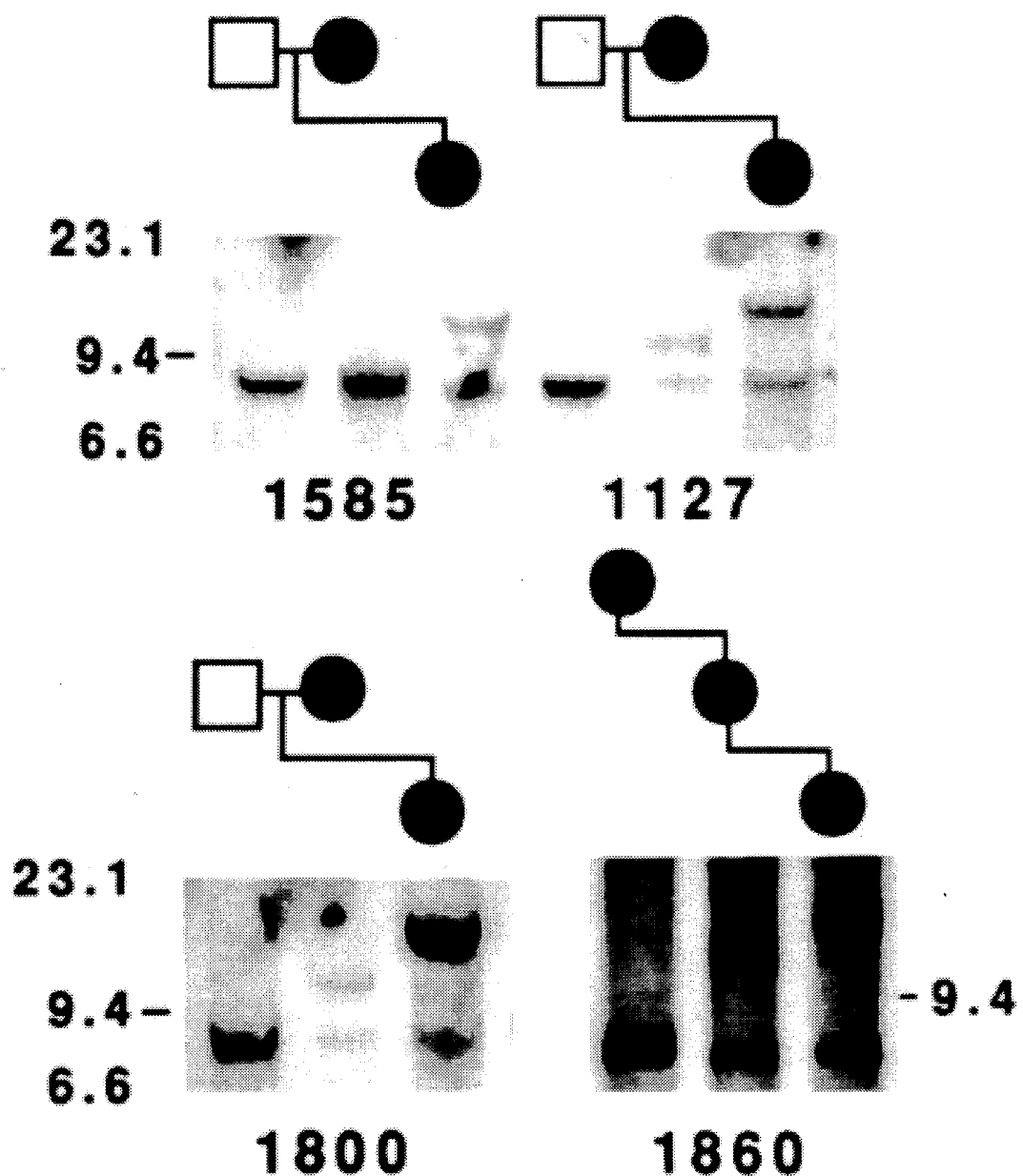
FIG. 3 shows Southern analysis of leukocyte DNA with probes containing the GCT repeat from pMDY1 and demonstrates that sequence expansion is the molecular alteration associated with myotonic dystrophy.

To test genetic instability at the DM locus by studying families with congenital DM born to affected DM mothers were studied. Evidence of genetic instability at the DM locus is illustrated in FIGS. 2–3. NcoI digestion and Southern Blot analysis was performed on samples from families in which a congenitally affected child has been born using the cloned 1.4 kb BamHI fragment from cosmid MDY1 as a probe (Families 1585, 1127, and 1800) or the mixed probe (1.4 kb and 1.35 kb BamHI fragments) (Family 1860). Sequence enlargement in each congenitally affected child was demonstrated. Sequence enlargement to a lesser extent was also detected in the affected mother from Families 1127 and 1800 and in an increasing pattern in the affected grandmother from Family 1860. Family 1860 in FIG. 3 shows an example where a three-generation transmission of DM exhibits progressive enlargement (8.8 kb to 12.7 kb) of an NcoI fragment.

After digestion with the 3 restriction enzymes indicated, probes comprised of the 1.4 kb and the 1.35 kb BamHI fragments from cosmid MDY1 clearly identified enlarged DNA fragments from the congenitally affected child born to the affected mother from Family 953. The enlarged sequence was detected in neither parent and, by examination of the BamHI data, is at least 6 kb larger than sequence detected in the parents. Other restriction endonucleases including BanI and TaqI also identified fragment enlargements (FIG. 2).

Further it was found that 9 of 9 congenital DM patients and 14 of 16 adult DM patients had fragment enlargements. An exception is shown in FIG. 3 (Family 1585). There were no fragment enlargements or reductions among 31 controls examined. Since each congenital DM patient had unique enlarged restriction fragments which cannot be attributed to the parents, it is concluded that this DNA sequence expansion is the mutational basis of DM. In each of these families non-parentage was excluded by the linkage study.

EXAMPLE 3

PCR Analysis 100 ng of genomic DNAs were mixed with 3 pmole of each primer (SEQ. ID. Nos. 2 and 3 ) in a total volume of 15 µl containing 10 mM Tris-HCl pH8.3, 50 mM KCL, 1.5 mM $MgCl_2$, 200 µM of each of the 4 dNTPs, 4 µCi of $^{32}$p-dCTP and 0.75 units of AmpliTaq DNA polymerase. The reactions were heated to 95° C. for 10 min. and followed by 25 cycles of denaturation (95° C., 1 min), DNA reannealing (54° C., 1 min), and elongation (72° C., 2 min). The radioactive PCR products were combined with 95% formamide loading dye and then heated to 95° .C. for 2 min before electrophoresis through a 6% denaturing DNA sequencing gel. Allele sizes were determined by their migration relative to an M13 sequencing ladder. For analysis by 3% agarose gel electrophoresis, 200 ng of genomic DNA was amplified in a final volume of 100 µl using the same buffer, 250 µM of the 4 dNTPs and 0.5 units of AmpliTaq DNA polymerase. The reactions were heated to 95° C. for 5 min and then subjected to 32 cycles of 94° C. for 1 min 57° C. for 1 min, and 72° C. for 3 min.

EXAMPLE 4

DNA Sequence Characterization

Figure 4:
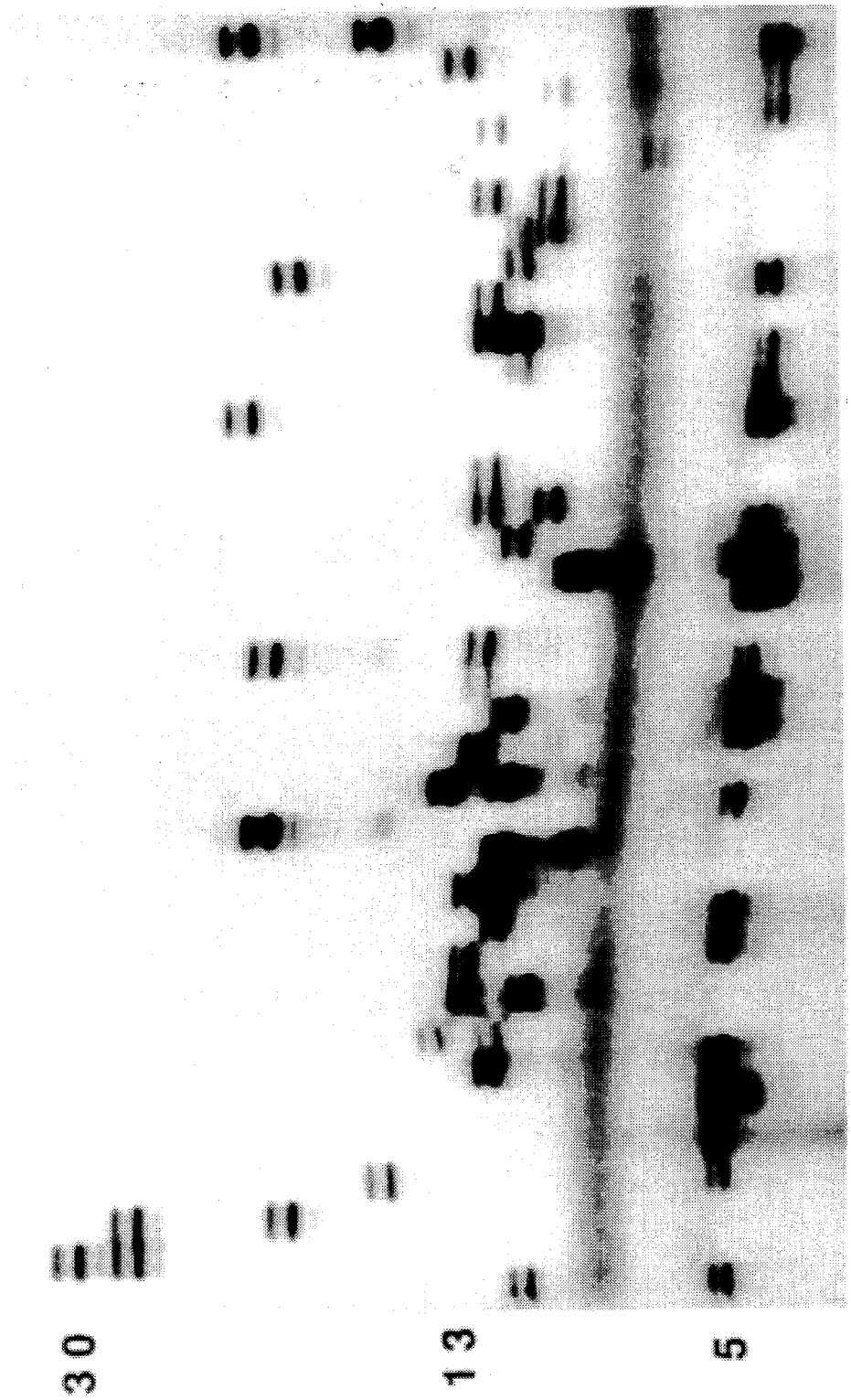
FIG. 4 shows the polymorphic nature of the GCT locus in normal human genomic DNAs. Amplification of genomic DNA was carried out as described in Example 3 and analyzed on a denaturing DNA sequencing gel.
Figure 5:
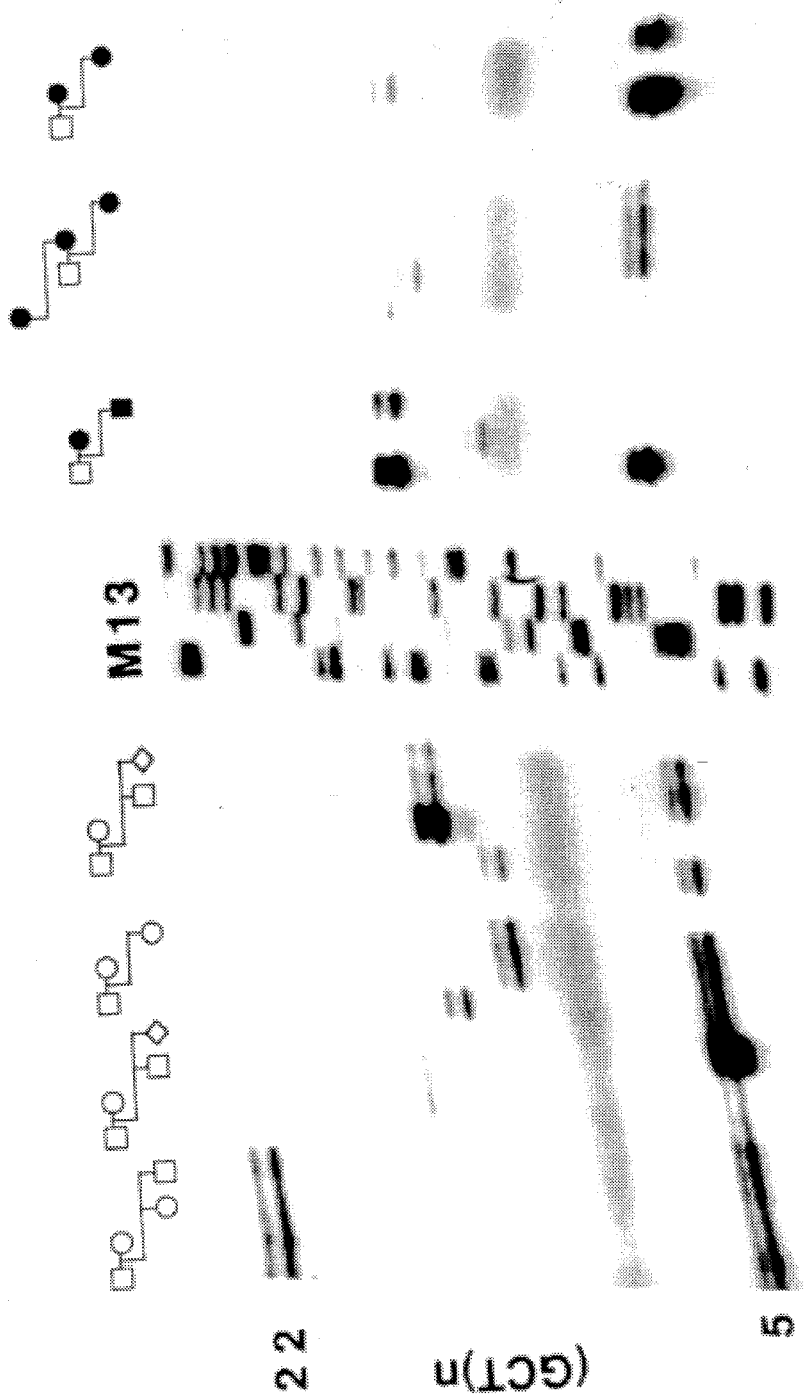
FIG. 5 shows the sequence based GCT alleles determined by PCR in control families and myotonic dystrophy families. Control families exhibit Mendelian inheritance of alleles. In myotonic dystrophy families, all affected individuals show only one allele, that from the normal parent.

In an effort to delineate the sequence involved in the DNA expansion, the GCT repeat size variation was examined using PCR amplification, followed by agarose and polyacrylamide gel electrophoresis. Using synthetic oligonucleotides which immediately flank the GCT repeat (FIG. 1), analysis of the radioactive amplification products indicated that the region is highly polymorphic (FIG. 4). The most common allele is 5 repeats with extremes of 5 to 30 from 40 normal individuals analyzed. The heterozygote frequency is 85%. This length polymorphism can also be observed by agarose gel analysis but with less detailed resolution. Examination of this sequence polymorphism in 3 DM and 4 control families is shown in FIG. 5. Unaffected individuals have the expected frequency of pairs of alleles, while DM patients have only one, the allele of the unaffected parent. Mendelian inheritance of alleles is observed in the control families. Thus, in these family studies, the DM GCT allele (as measured by PCR) is not detectable. Southern analysis indicates that each affected individual has a large expanded fragment. A repeat sequence of longer than 3 kb is beyond current ability to amplify using PCR. The simplest interpretation of these data is that the GCT repeat has meiotic instability at the DM locus and is responsible for the mutation in DM. Examination by PCR of the regions immediately flanking the GCT repeats indicated in FIG. 1 shows them to be non-polymorphic and unaltered in DM families.

EXAMPLE 5

Since both the FMR-1 (Fragile X) and androgen receptor (Kennedy) mRNA contain triplet repeats, the pMDY1 sequence was examined by the computer program Grail (Gene Recognition and Analysis Internet Link). GRAIL Computer searches are available to general users by the Oak Ridge National Laboratory File server at GRAIL@ornl.gov. This program revealed an "excellent" exon identification score possibly biased by the inclusion of triplet repeat sequences. The transcript was directly searched using brain and skeletal muscle mRNA copied by reverse transcriptase (cDNA). This study identified amplified products of the expected size supporting the computer prediction. Furthermore, the pMDY1 probe successfully identified brain cDNA clones whose GCT repeat alleles differed. These data collectively indicate the repeat sequence is in a gene.

EXAMPLE 6

Figure 6:
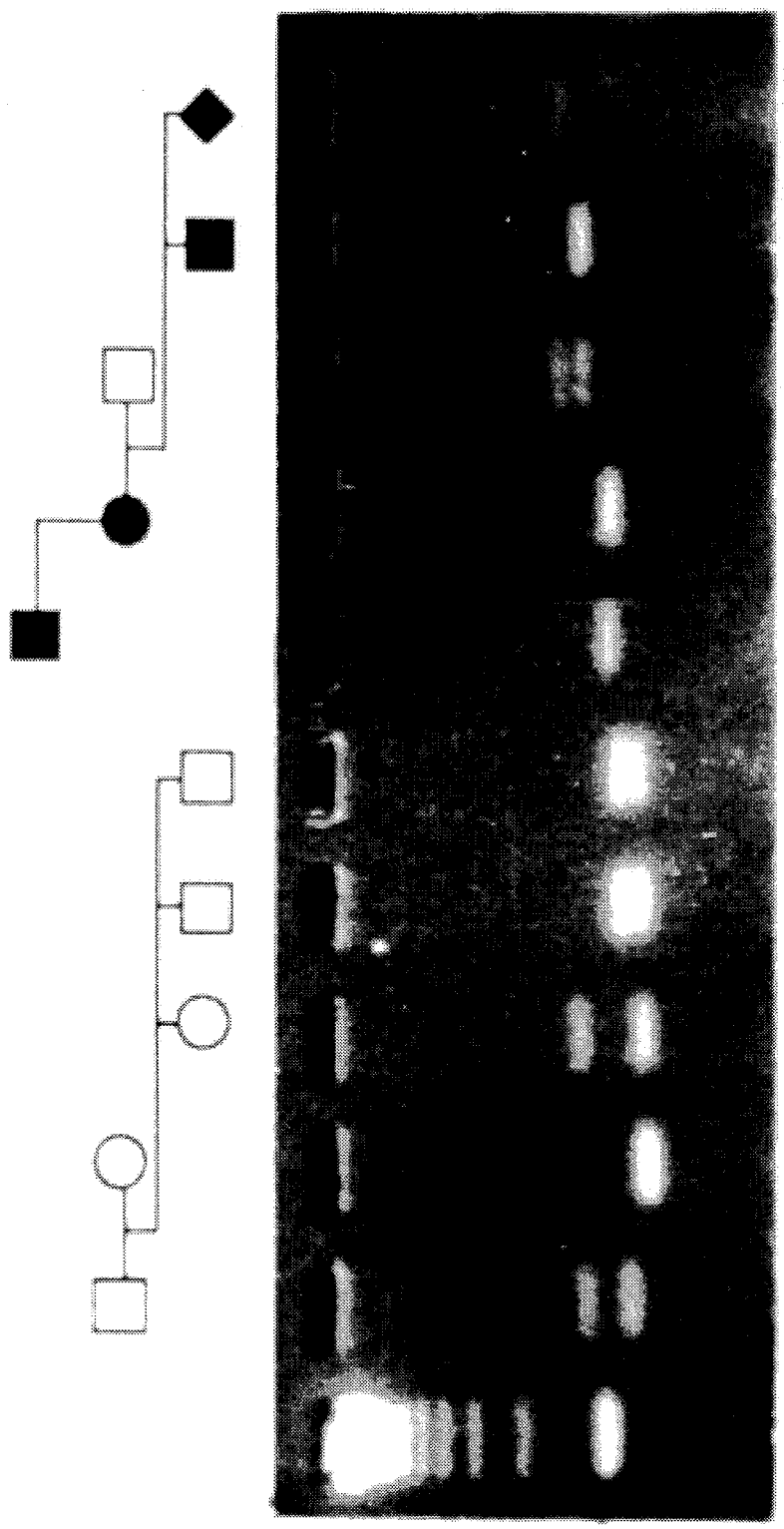
FIG. 6 shows prenatal diagnosis of myotonic dystrophy using PCR analysis of the GCT repeat locus from MDY1. The control family is on the left and the filled symbols represent affected individuals. The size standard in the left lane is a 123 bp ladder.

The utility of DNA-based detection of DM mutations is illustrated by prenatal diagnosis. In this pregnancy, the fetus was predicted to have a greater than 97% risk to be affected on the basis of linkage analysis. The result from the family is shown in FIG. 6. Amplification of the polymorphic region using DNA extracted from leukocytes or cultured chorionic villi cells and the oligonucleotide primers shown in FIG. 1 followed by electrophoresis through a 3% agarose gel identified a Mendelian pattern of inheritance of the informative paternal PCR amplified GCT alleles in a control family (left). All individuals affected with myotonic dystrophy (filled symbols) appeared to be hemizygous (or homozygous) for the GCT locus. A maternal allele was not detected in the congenitally affected child. The fetus, which had been judged to be at greater than 97% risk to be affected by linkage analysis, inherited the opposite paternal allele and was confirmed to be affected by the absence of an amplifiable maternal allele. Thus, direct detection of the DM mutation by PCR was in agreement with the linkage prediction. This procedure which is an additional DNA-based method for diagnosis of DM utilizes direct mutation detection. It provides greater ease and accuracy.

EXAMPLE 7

Detecting Triplet Repeat Mutations

The synthetic oligonucleotides of GC rich triplet character as shown in FIG. 7 were used in a scanning strategy to identify unstable genetic sequences. Oligonucleotides were labelled with gamma-$^{32}$P-ATP at the 5' end and used as probes to screen libraries which can be cDNA, cosmid, lamda, and plasmid genomic libraries. The scanning procedure detected a highly polymorphic GCT repeat at the DM locus. This repeat was characterized. It identified an unstable and expanding sequence found in DM patients. In FIG. 7 is shown the GC rich triplets useful in scanning for autosomal disease.

EXAMPLE 8

Gene Structure and Isoforms of Mt-PK Gene

Figure 8:
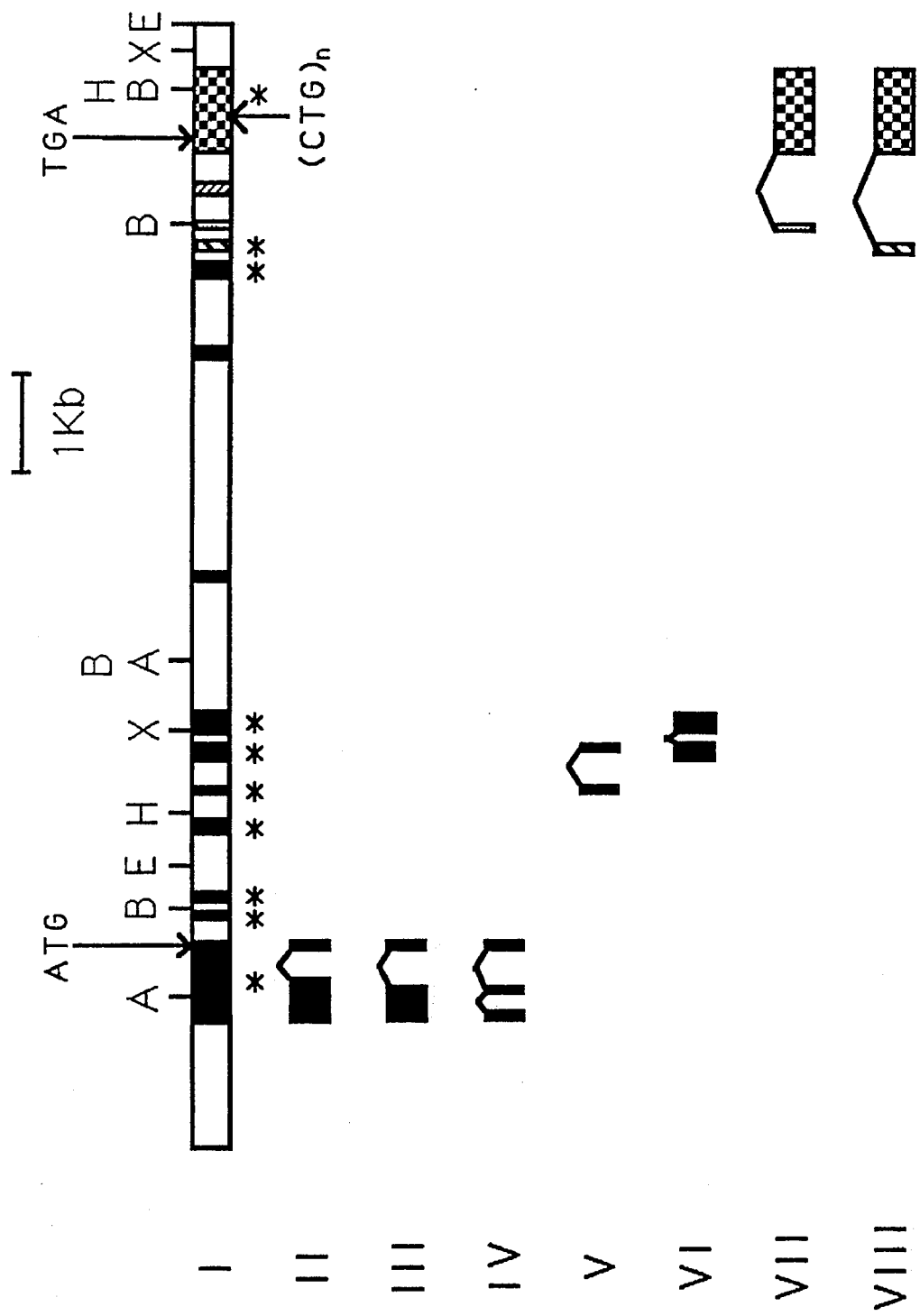
FIG. 8 shows the gene structure of Mt-PK and various isoforms of Mt-PK mRNA. Filled and patterned boxes indicate the locations of exons. The exons that coincide with the prediction by GRAIL as described in Example 5 are shown with asterisks beneath. All the exons predicted by GRAIL with excellent scores coincide with real exon positions. All the mRNA isoforms were obtained as described in Example 8. In the isoforms II–VIII, only the exons involved in the changes are shown. Isoforms II, III and IV are alternatively spliced variants of form I. Restriction enzymes: A-XbaI, B-BamHI, E-EcoRI, H-HindIII, X-XhoI.

The genomic sequence of MT-Pk was determined from M13 subclones of a cosmid clone found to contain the structural gene on the basis of homology to the MT-Pk cDNA and GCT repeat. A graphic representation of the gene is given in FIG. 8. Grail computer analysis of this sequence identified putative exons which are illustrated in FIG. 8 for sequences whose score was "excellent". Additional exons were identified from the cDNA clones and from that of alternative splice forms determined by sequence of reverse transcriptase PCR (RTPCR). The RTPCR sequences were obtained from human adult muscle, brain and heart tissues while the cDNA clone was obtained from brain tissue. The alternative splice forms are graphically represented in FIG. 8. In each case the RT cDNA sequence was determined by automated DNA sequencing from plasmid subclone of the PCR product. Each isoform was amplified from muscle or heart mRNA using primers from exons flanking the intron sequence to avoid nuclear DNA amplification products. Eight alternative splice forms which differ primarily in the 5' and 3' regions of the mRNA of MT-Pk have been identified. In all cases, protein kinases sequence homology (located in exons 2–6) is preserved and not affected by the alternative splice events. Several interesting splice forms would suggest deleted (Forms V, VI, VII, and VIII) or alternate coding sequence (Form VIII) for the MT-Pk. Form VIII lacks both exons 12 and 13. This generates a termination codon immediately after the splice acceptor which removes a predicted carboxyl-terminal transmembrane domain of the protein.

EXAMPLE 9

Development of Antibodies for Mt-PK Protein

Figure 9:
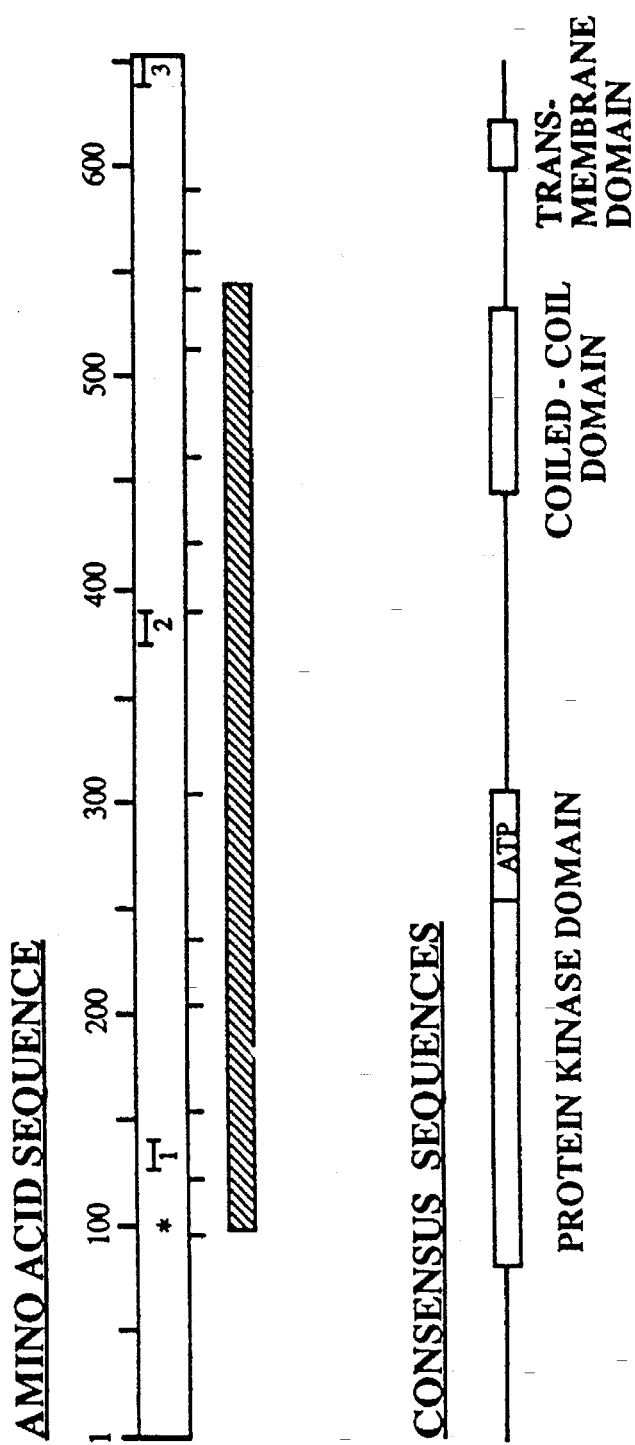
FIG. 9 shows synthetic peptide locations (shown as a line under the amino acid sequence positions) and consensus regions of Mt-PK. The hatched box indicates the truncated protein expressed in E. coli. The corresponding number of antibody to synthetic peptide is: SEQ. ID. NO. 7–9828, SEQ. ID. NO. 8–254, SEQ. ID. NO. 9–10257.
Figure 10:
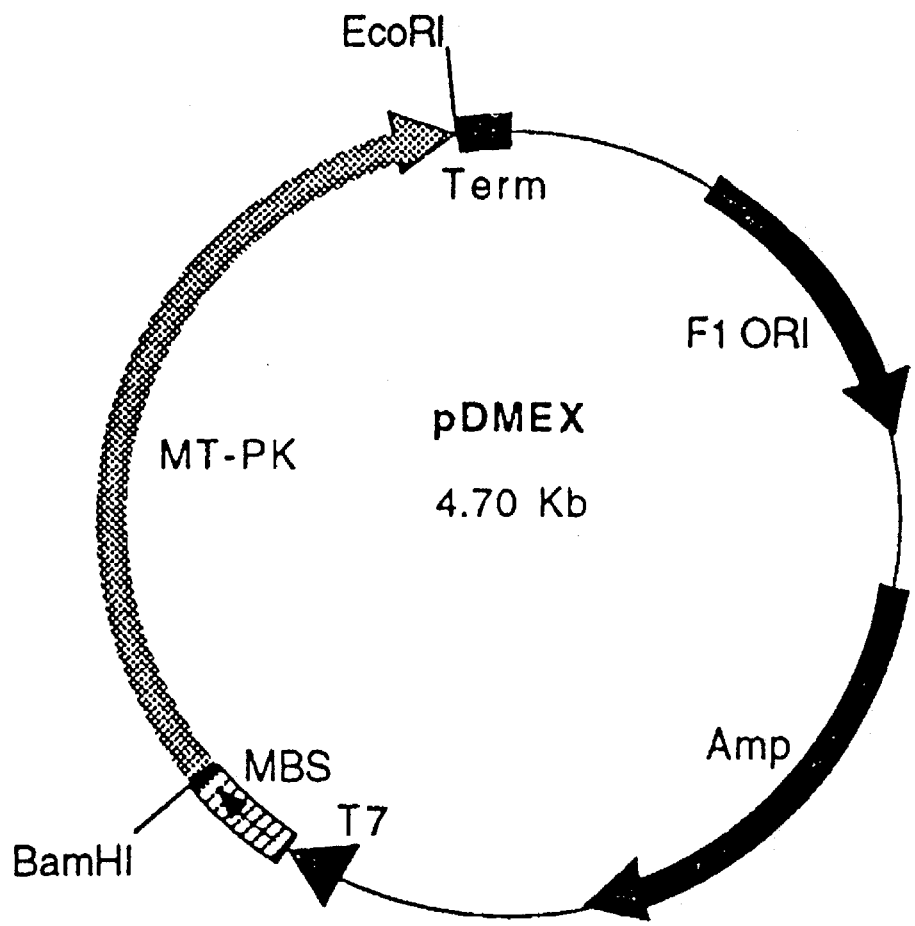
FIG. 10 shows the plasmid map for the construct which express myotonic protein kinase in bacteria.

In an effort to understand better the Mt-PK protein isoforms, antibodies were developed to both synthetic peptides and purified Mt-PK protein expressed in *E. coli*. Antibodies were developed against synthetic peptide immunogens (SEQ. ID. NOS. 7,8 and 9) using selected amino acid sequences of Mt-PK as designated on FIG. 9. Three antipeptide antisera (9828, 10257, 254) were generated that recognize a 55,000 molecular weight protein in muscle, the expected size of the Mt-PK. In addition to antipeptide antibodies, we developed a specific and high affinity antibody (10033) using as antigen a truncated Mt-PK protein produced with the prokaryotic expression vector pRSET (Invitrogen Co.). This construct (as shown in FIG. 10) incorporated the isoform VIII 3' termination codon and was devoid of the Mt-PK putative membrane spanning domain. In addition, the metal binding domain of the pRSET vector was fused in-frame at the amino terminus of Mt-PK with the AUG of bp 842. This recombinant vector provided a chimeric peptide that was subsequently purified by nickel affinity chromatography. Following purification of the expressed protein on a nickel column, N-terminal amino acid sequencing was carried out to verify the identity of the purified product. The sequence obtained corresponded to the nickel binding epitope, followed by four residues of the Mt-PK sequence initiating with methionine encoded at bp 842 (M-K-Q-T), confirming the authenticity of the chimeric Mt-PK protein. The fusion protein was then used to validate the specificity of antibodies raised against peptides and the prokaryotically expressed antigen.

EXAMPLE 10

Western Blot Analysis

Figure 11:
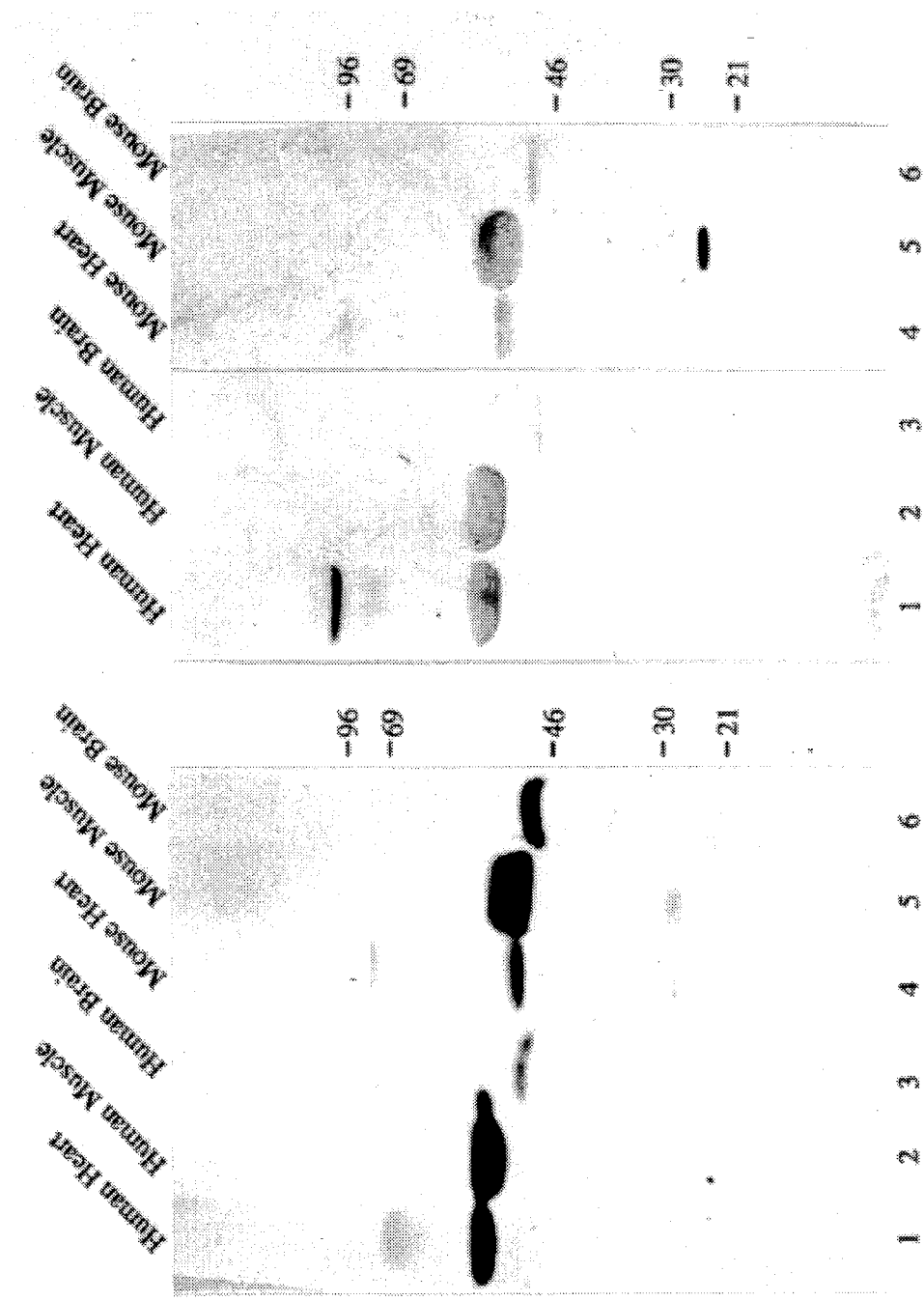
FIG. 11 shows western blot analysis of human and mouse tissues with the myotonic protein kinase antibody. The rodent Mt-PK isoforms run at lower apparent molecular weight (52,000) than the human isoforms.

We have used these antibodies (10033 and 254) to detect proteins by western analysis in selected tissues (FIG. 11). These studies indicate a high level of Mt-PK protein expression in both human and rodent muscle, heart and to a lesser extent in brain. Human and mouse tissues were disrupted in isotonic buffer containing protease inhibitors and spun at

EXAMPLE 11

Quantitation of MT-PK mRNA

Figure 12:
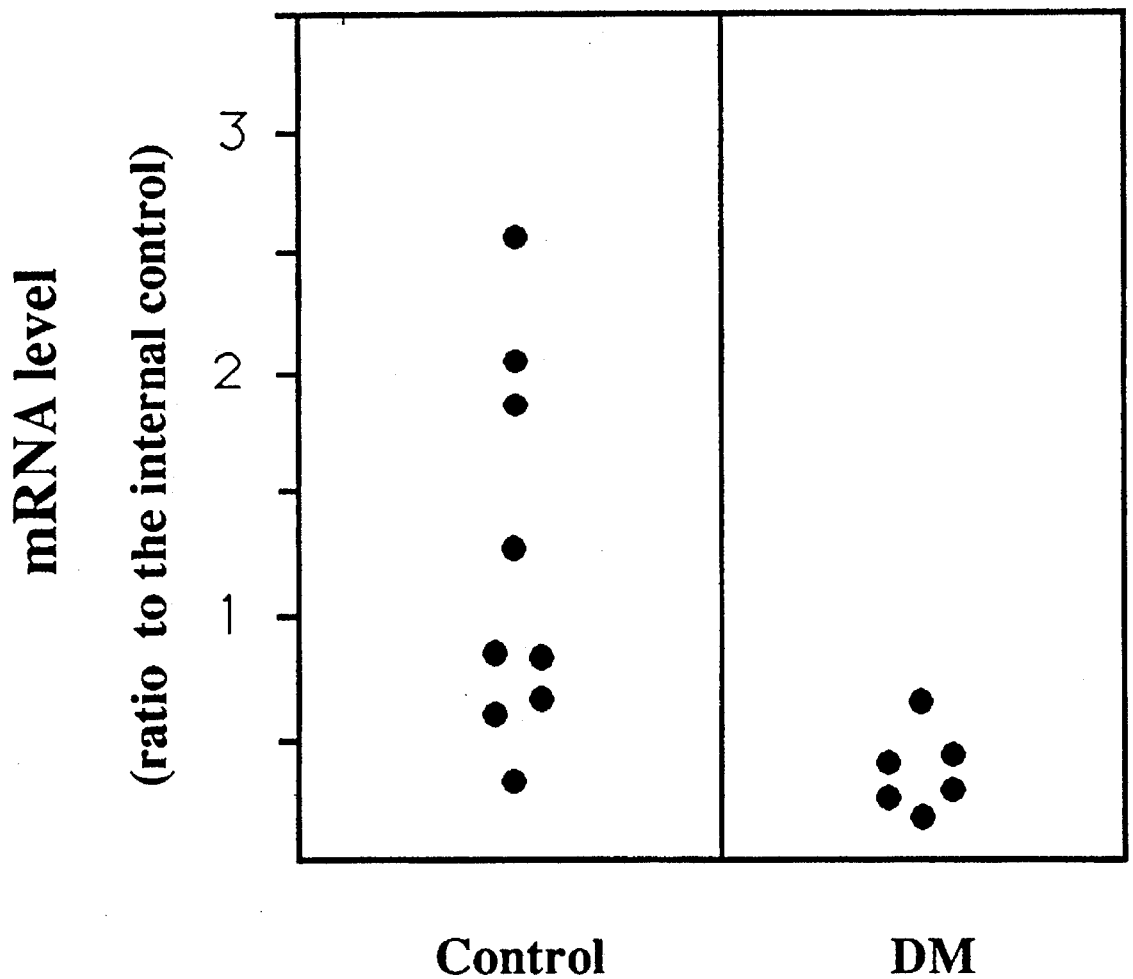
FIG. 12 shows quantitation of mRNA levels for normal and DM adult patients by RTPCR (reverse transcriptase PCR). Each dot represents the average of nine determinations which were carried out as described in Example 11 for each RNA sample. The numbers shown here are the ratio of the Mt-PK RTPCR product to the internal control, human transferrin receptor, RTPCR product.

In order to determine if the CTG repeat expansion altered the level of the mRNA in tissues, we developed a quantitative RTPCR assay. Total RNA was extracted from various tissues by RNAzol. 1 ug of total RNA was used for the reverse transcription reaction using Superscript RT (BRL) following the manufacturer's instructions. The reverse transcription reaction was heat terminated and diluted 2.5X with $H_2O$. 2 ul of the RT product were then used for the PCR reaction which used two sets of primers; one set for the Mt-PK gene (SEQ. ID. Nos. 12 and 13) and one set for the human transferrin receptor gene (an internal control) (SEQ. ID. Nos. 4 and 5). The PCR products were analyzed on a 2% agarose gel and scanned by a Gene Scanner (ABI). mRNA of transferrin receptor (TFR), a stably-expressed gene, was used as an internal quantitation standard. The ratio of Mt-PK/TFR for different individuals and clinical conditions is given in FIG. 12. In adults with myotonic dystrophy the mRNA levels were found to be consistently low. Using primer pairs which permit a distinction between the two different alleles (i.e. primers flanking the CTG repeats) it was found that the mRNA level of the mutant allele from the adult DM expressed at lower levels—i.e. lack of coequal expression of wild type and mutant mRNA.

EXAMPLE 12

PCR-Southern Analysis of mRNA Level

Figure 13:
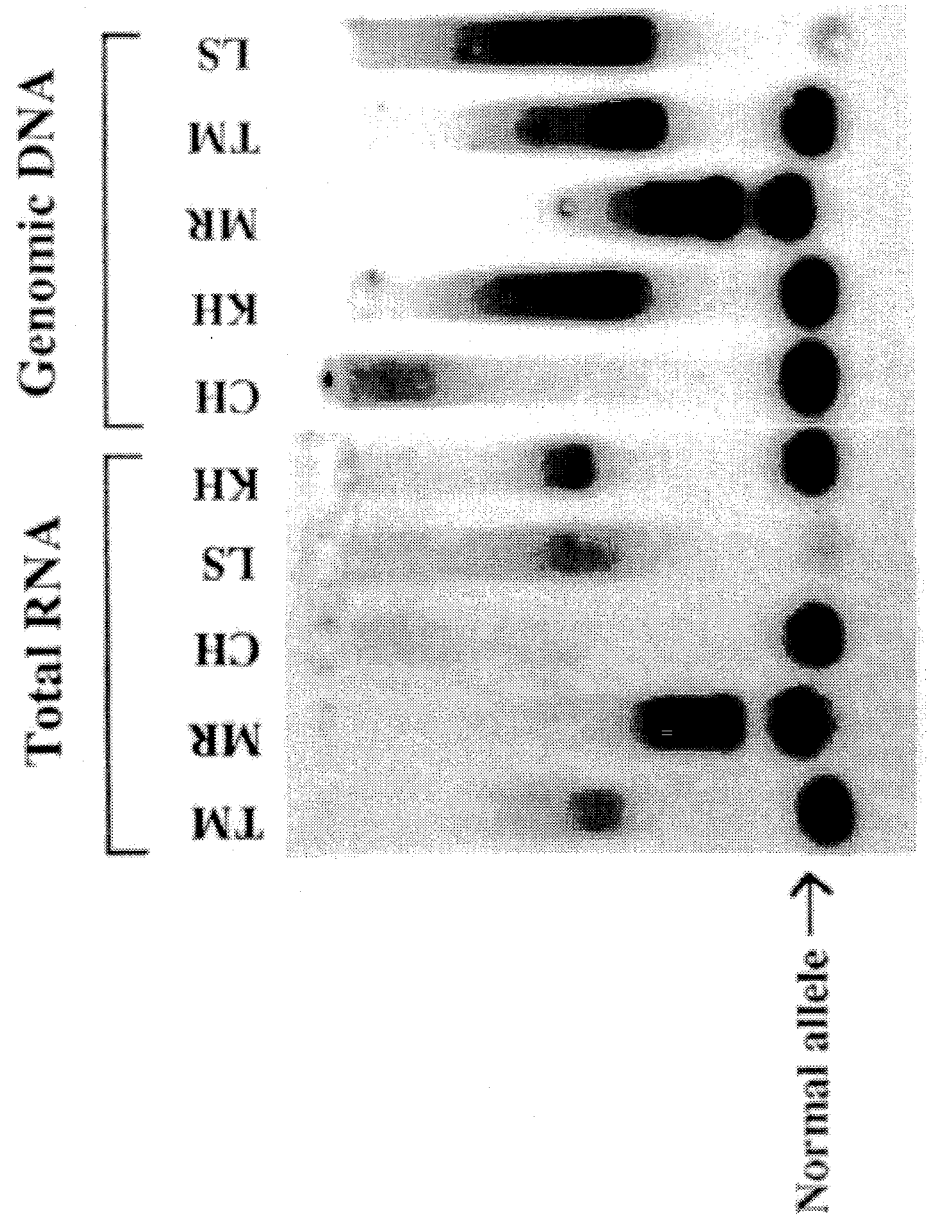
FIG. 13 Southern blot for PCR products from genomic DNA and total RNA. The mutant allele GCT repeat sizes for these samples are: TM-120, MR-68(the smallest one), LS-160, KH-205, CH-800.

Genomic DNA and total RNA were isolated from lymphoblastoid cell lines. RNA was treated with DNaseI before RTPCR reaction. PCR primers flanking the CTG repeat were used and PCR products were loaded onto 2% agarose gel. Oligonucleotide of 21 residues in length was used as probe for the Southern analysis. We were able to detect the mRNA level of normal alleles, reduced levels from permutation alleles (up to 205 repeats), and at extremely low levels from mutant allele with 800 repeats (See FIG. 13). Genomic DNA with the same number of repeats were used as the control for evaluating PCR efficiency. Thus, in adult DM, the level of mRNA identified by the RTPCR was mostly to fully accounted for by the normal Mt-PK alleles. These observations contrast with our coequal detection of two normal alleles in the control individuals.

EXAMPLE 13

Quantitation of Mt-PK Protein by Radioimmunoassay (RIA)

Figure 14:
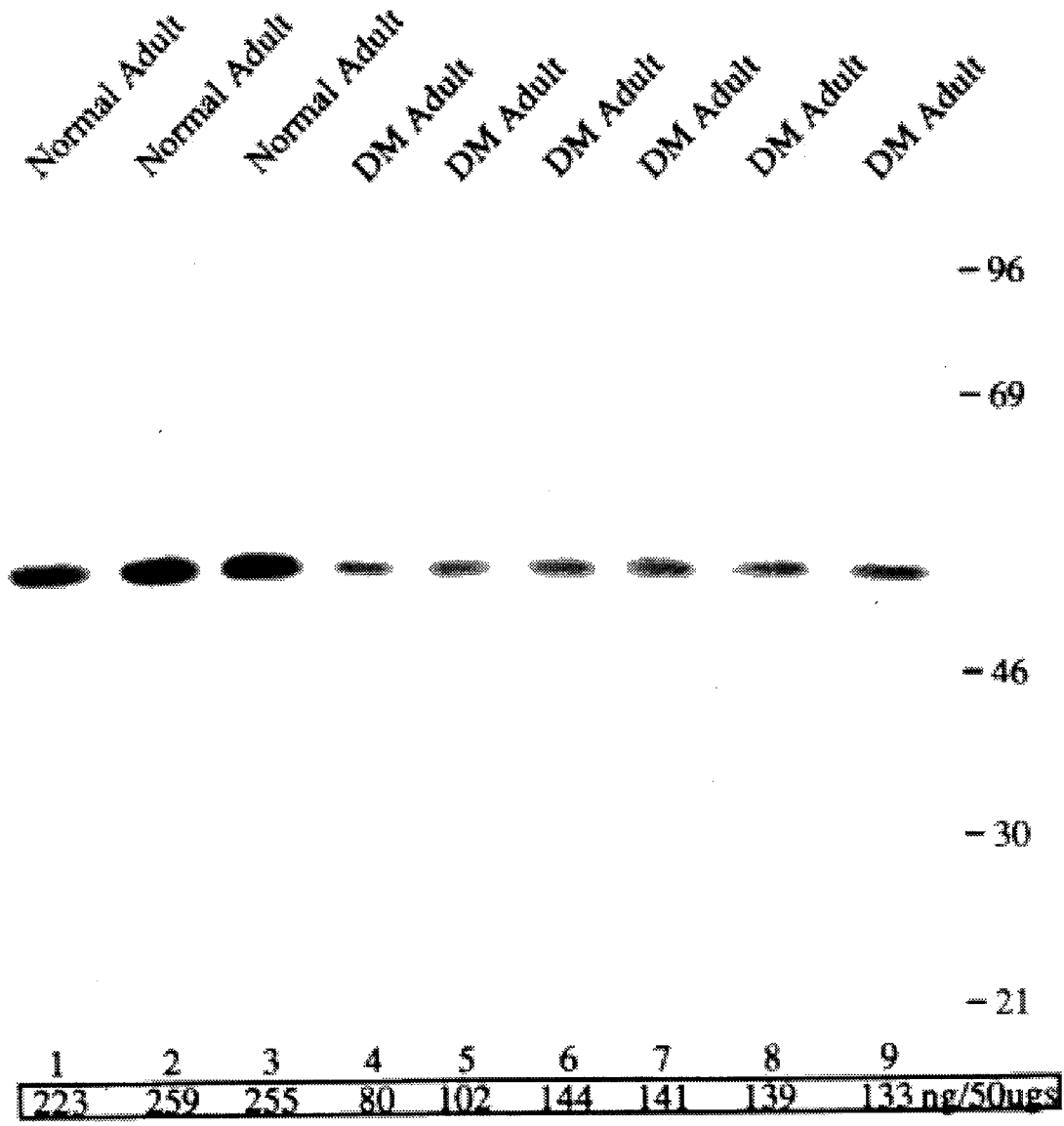
FIG. 14 Evaluation of Mt-PK protein expression in adult muscle. Skeletal muscle biopsies from normal individuals and DM patients were processed for western blots as described in Example 10. Exactly 50 µg total protein was loaded per lane. The numbers below the lanes show the amount of Mt-PK detected in the samples by RIA as described in Example 13. The reported values are the mean from triplicate determinations. The values were expressed as ng/50 µg tissue protein.
Figure 15:
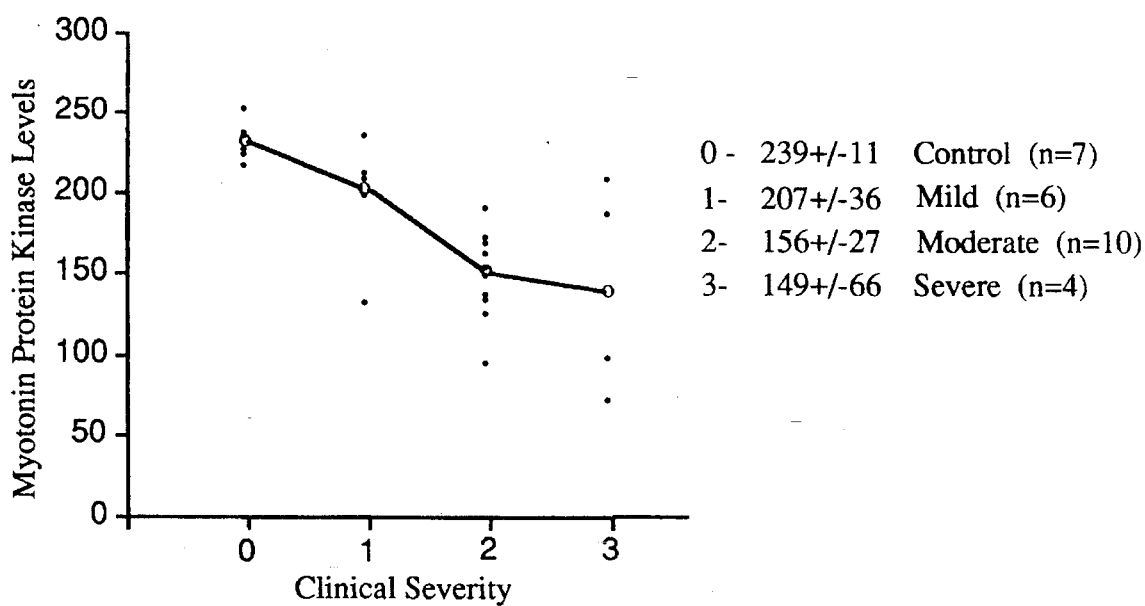
FIG. 15 shows the correlation between Mt-PK protein levels and the disease severity of adult DM.

The level of Mt-PK protein has been determined in normal and diseased adult muscle by two methods, western blot and radioimmunoassay (RIA). Tissue extracts (1 to 10 ug) were incubated with $^{125}$I-labelled Mt-PK fusion protein (7 uCi/ug protein) and anti Mt-PK antisera (10033, at a final dilution of 1/1000), for 2 hours at room temperature. The immune complex was precipitated with protein A agarose for 45 minutes. The precipitate was washed three times with buffer containing Tris-HCl (pH8.3), 1% NP-40, 3% BSA, and 0.5M NaCl. The relative level of Mt-PK in adult muscle is shown in FIG. 14. A total 20 DM patients and 7 normal individuals were examined. Decreased Mt-PK expression was found in 18 out of 20 adult patients, and the amount of the decrease was proportional to the severity of disease as shown in FIG. 15. Thus, by two independent methods the Mt-PK gene expression has been shown to be decreased in adult DM muscle compared to normal adult muscle.

---

What is claimed is:

1. A method of screening, whereby individuals at risk for developing DM are identified, said method comprising the steps of:
digesting DNA from an individual to be tested with a restriction endonuclease; and
measuring the length of a restriction fragment length polymorphism (RFLP) with hybridization to probes that recognize a $(GCT)_n$ repeat at the 3' end of a DM locus and southern blot analysis.

2. The method of claim 1 wherein the restriction endonuclease is selected from the group consisting of Ban1, Taq1, and Nco1.

3. The method of claim 1 wherein the probe is pMDY1 or a fragment thereof.

4. A method of screening, whereby individuals at risk for developing DM are identified, said method comprising the steps of measuring expression of a DM gene by determining an amount of mRNA expressed from the DM gene and from known controls, and comparing the amount of mRNA from the DM gene to the amount from the known controls.

5. The method of claim 4, wherein the mRNA is determined by the steps of:
extracting RNA from individuals to be tested;
preparing cDNA from myotonic protein kinase (Mt-PK) gene and a control gene; and
quantification by comparison of Mt-PK with a control gene.

6. The method of claim 5, wherein the quantification step includes PCR of the Mt-PK cDNA and PCR of a control gene cDNA to produce PCR products, electrophoresis of the PCR products, ethidium bromide staining of the products and quantification of Mt-PK products versus control gene products.

7. The method of claim 6, wherein oligonucleotide primers SEQ. ID. No. 12 and SEQ. ID. No. 13 are used to amplify the Mt-PK cDNA.

8. The method of claim 6, wherein the control gene cDNA is a cDNA from human transferrin receptor gene and oligonucleotide primers SEQ. ID. No. 4 and SEQ. ID. No. 5 are used to amplify said transferrin receptor gene cDNA.

9. A method to detect a mutation at a DM locus comprising the step of detecting variation of $(GCT)_n$ repeats at the 3' end of a Mt-PK gene by measuring the length of the repeat, wherein the number of repeats for normal ranges between 5 and 33, and the number of repeats for DM is greater than 35.

10. The method of claim 9, wherein the size of repeat is determined by pulsed field gel electrophoresis.

11. The method of claim 9 wherein the size of the repeat is determined by dosage measurements of Southern blotting analysis of restriction enzyme digests with probes contained within the Mt-PK gene region.

12. The method of claim 9, wherein the variation of the $(GCT)_n$ repeat is measured by PCR.

13. The method of claim 12, wherein oligonucleotide primers SEQ. ID. No. 2 and SEQ. ID. No. 3 are used in the PCR reaction.

14. The method of claim 12, comprising the steps of:
extracting DNA from an individual to be tested;
amplifying said DNA by PCR analysis using oligonucleotide primers consisting of SEQ. ID. Nos. 2 and 3;
measuring the size of the amplified product, wherein a size of greater than 50 GCT repeats or a lack of amplification products in addition to products from a normal allele indicates a presence of DM disease.

15. A method of detecting a length of a GCT polymorphism at a 3' end of a Mt-PK gene comprising the steps of performing a PCR assay with oligonucleotide primers to produce amplified products and measuring the length of the amplified products, wherein the oligonucleotide primers are SEQ. ID. No. 2 and SEQ. ID. No. 3.

16. A method of screening, whereby individuals at risk for developing autosomal genetic disease are identified, said method comprising the steps of detecting variation of a GC-rich triplet repeats at the 3' end of a gene by measuring the length of the repeat wherein the number repeats for normal ranges between 5 and 33 and the number of repeats for diseased is greater than 35.

17. A cosmid probe to a $(GCT)_n$ repeat derived from YAC clones 231G8 and 483E7 which cover the DM genomic region.

* * * * *

Adverse Decisions In Interference

Patent No. 5,552,282, C. Thomas Caskey, Ying Hui-Fu, David L. Friedman, Antonio Pizzuti, Raymond G. Fenwick, DIAGNOSIS OF MYOTONIC MUSCULAR DYSTROPHY, Interference No. 103,978, final judgment adverse to the patentees rendered July 20, 1998, as to claims 1-16.
*(Official Gazette October 27, 1998)*

Adverse Decisions In Interference

Patent No. 5,552,282, C. Thomas Caskey, Ying Hui-Fu, David L. Friedman, Antonio Pizzuti, Raymond G. Fenwick, DIAGNOSIS OF MYOTONIC MUSCULAR DYSTROPHY, Interference No. 103,977, final judgment adverse to the patentees rendered July 20, 1998, as to claim 17.
*(Official Gazette October 27, 1998)*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1383 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GGATCCACCT  TCCCATGTAA  GACCCTCTC   TTTCCCCTGC  CTCAGACCTG  CTGCCCATTC     60

TGCAGATCCC  CTCCCTGGCT  CCTGGTCTCC  CCGTCCAGAT  ATAGGGCTCA  CCCTACGTCT    120

TTGCGACTTT  AGAGGGCAGA  AGCCCTTTAT  TCAGCCCCAG  ATCTCCCTCC  GTTCAGGCCT    180

CACCAGATTC  CCTCCGGGAT  CTCCCTAGAT  AACCTCCCCA  ACCTCGATTC  CGCTCGCTGT    240

CTCTCGCCCC  ACCGCTGAGG  GCTGGGCTGG  GCTCCGATCG  GGTCACCTGT  CCCTTCTCTC    300
```

| | | | | | | |
|---|---|---|---|---|---|---|
| TCCAGCTAGA | TGGCCCCCCG | GCCGTGGCTG | TGGGCCAGTG | CCCGCTGGTG | GGGCCAGGCC | 360 |
| CCATGCACCG | CCGCCACCTG | CTGCTCCCTG | CCAGGGTACG | TCCGGCTGCC | CACGCCCCC | 420 |
| TCCGCCGTCG | CGCCCCGCGC | TCCACCCGCC | CCGTGCCACC | CGCTTAGCTG | CGCATTTGCG | 480 |
| GGGCTGGCC | CACGGTAGGA | GGGCGGATCT | TCGGGCAGAC | AATCAACACA | GGCCGCTAGG | 540 |
| AAGCAGCCAA | TGACGAGTTC | GGACGGGATT | CGAGGCGTGC | GAGTGGACTA | ACAACAGCTG | 600 |
| TAGGCTGTTG | GGGCGGGGGC | GGGGCGCAGG | GAAGAGTGCG | GGCCCACCTA | TGGGCGTAGG | 660 |
| CGGGGCGAGT | CCCAGGAGCC | AATCAGAGGC | CCATGCCGGG | TGTTGACCTC | GCCCTCTCCC | 720 |
| CGCAGGTCCC | TAGGCCTGGC | CTATCGGAGG | CGCTTTCCCT | GCTCCTGTTC | GCCGTTGTTC | 780 |
| TGTCTCGTGC | CGCCGCCCTG | GGCTGCATTG | GGTTGGTGGC | CCACGCCGGC | CAACTCACCG | 840 |
| CAGTCTGGCG | CCCGCCCAGG | AGCCGCCCGC | GCTCCCTGAA | CCCTAGAACT | GTCTTCGACT | 900 |
| CCGGGGCCCC | GTTGGAAGAC | TGAGTGCCCG | GGGCACGGCA | CAGAAGCCGC | GCCCACCGCC | 960 |
| TGCCAGTTCA | CAACCGCTCC | GAGCGTGGGT | CTCCGCCCAG | CTCCAGTCCT | GTGACCGGGC | 1020 |
| CCGCCCCTA | GCGGCCGGGG | AGGGAGGGGC | CGGGTCCGCG | GCCGGCGAAC | GGGGCTCGAA | 1080 |
| GGGTCCTTGT | AGCCGGGAAT | GCTGCTGCTG | CTGCTGCTGC | TGCTGCTGCT | GCTGGGGGA | 1140 |
| TCACAGACCA | TTTCTTTCTT | TCGGCCAGGC | TGAGGCCCTG | ACGTGGATGG | GCAAACTGCA | 1200 |
| GGCCTGGGAA | GGCAGCAAGC | CGGGCCGTCC | GTGTTCCATC | CTCCACGCAC | CCCCACCTAT | 1260 |
| CGTTGGTTCG | CAAAGTGCAA | AGCTTTCTTG | TGCATGACGC | CCTGCTCTGG | GGAGCGTCTG | 1320 |
| GCGCGATCTC | TGCCTGCTTA | CTCGGGAAAT | TTGCTTTTGC | CAAACCCGCT | TTTTCGGGGA | 1380 |
| TCC | | | | | | 1383 |

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

GCTCGAAGGG TCCTTGTAGC CGGG    24

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

CTGGCCGAAA GAAAGAAATG GTC    23

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

CAGCTCCCTG AATAGTCCAA GTAG    24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

GAATTGAACC TGGACTATGA GAGG    24

( 2 ) INFORMATION FOR SEQ ID NO:6:

( i ) SEQUENCE CHARACTERISTICS:
        ( A ) LENGTH: 555 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Met Lys Gln Thr Gly Gln Val Tyr Ala Met Lys Ile Met Asn Lys Trp
 1               5                  10                  15

Asp Met Leu Lys Arg Gly Glu Val Ser Cys Phe Arg Glu Glu Arg Asp
                20                  25                  30

Val Leu Val Asn Gly Asp Arg Arg Trp Ile Thr Gln Leu His Phe Ala
            35                  40                  45

Phe Gln Asp Glu Asn Tyr Leu Tyr Leu Val Met Glu Tyr Tyr Val Gly
        50                  55                  60

Gly Asp Leu Leu Thr Leu Leu Ser Lys Phe Gly Glu Arg Ile Pro Ala
65                  70                  75                  80

Glu Met Ala Arg Phe Tyr Leu Ala Glu Ile Val Met Ala Ile Asp Ser
                85                  90                  95

Val His Arg Leu Gly Tyr Val His Arg Asp Ile Lys Pro Asp Asn Ile
            100                 105                 110

Leu Leu Asp Arg Cys Gly His Ile Arg Leu Ala Asp Phe Gly Ser Cys
        115                 120                 125

Leu Lys Leu Arg Ala Asp Gly Thr Val Arg Ser Leu Val Ala Val Gly
    130                 135                 140

Thr Pro Asp Tyr Leu Ser Pro Glu Ile Leu Gln Ala Val Gly Gly Gly
145                 150                 155                 160

Pro Gly Thr Gly Ser Tyr Gly Pro Glu Cys Asp Trp Trp Ala Leu Gly
                165                 170                 175

Val Phe Ala Tyr Glu Met Phe Tyr Gly Gln Thr Pro Phe Tyr Ala Asp
                    180                 185                 190

Ser Thr Ala Glu Thr Tyr Gly Lys Ile Val His Tyr Lys Glu His Leu
            195                 200                 205

Ser Leu Pro Leu Val Asp Glu Gly Val Pro Glu Glu Ala Arg Asp Phe
        210                 215                 220

Ile Gln Arg Leu Leu Cys Pro Pro Glu Thr Arg Leu Gly Arg Gly Gly
225                 230                 235                 240

Ala Gly Asp Phe Arg Thr His Pro Phe Phe Phe Gly Leu Asp Trp Asp
                245                 250                 255

Gly Leu Arg Asp Ser Val Pro Pro Phe Thr Pro Asp Phe Glu Gly Ala

-continued

|  |  |  | 260 |  |  |  |  | 265 |  |  |  |  | 270 |  |  |
|---|---|---|---|---|---|---|---|---|---|---|---|---|---|---|---|
| Thr | Asp | Thr 275 | Cys | Asn | Phe | Asp 280 | Leu | Val | Glu | Asp | Gly 285 | Leu | Thr | Ala | Met |
| Val | Ser 290 | Gly | Gly | Gly | Glu | Thr 295 | Leu | Ser | Asp | Ile | Arg 300 | Glu | Gly | Ala | Pro |
| Leu 305 | Gly | Val | His | Leu | Pro 310 | Phe | Val | Gly | Tyr | Ser 315 | Tyr | Ser | Cys | Met | Ala 320 |
| Leu | Arg | Asp | Ser | Glu 325 | Val | Pro | Gly | Pro | Thr 330 | Pro | Met | Glu | Leu | Glu 335 | Ala |
| Glu | Gln | Leu | Leu 340 | Glu | Pro | His | Val | Gln 345 | Ala | Pro | Ser | Leu | Glu 350 | Pro | Ser |
| Val | Ser | Pro 355 | Gln | Asp | Glu | Thr | Ala 360 | Glu | Val | Ala | Val | Pro 365 | Ala | Ala | Val |
| Pro | Ala 370 | Ala | Glu | Ala | Glu | Ala 375 | Glu | Val | Thr | Leu | Arg 380 | Glu | Leu | Gln | Glu |
| Ala 385 | Leu | Glu | Glu | Glu | Val 390 | Leu | Thr | Arg | Gln | Ser 395 | Leu | Ser | Arg | Glu | Met 400 |
| Glu | Ala | Ile | Arg | Thr 405 | Asp | Asn | Gln | Asn | Phe 410 | Ala | Ser | Gln | Leu | Arg 415 | Glu |
| Ala | Glu | Ala | Arg 420 | Asn | Arg | Asp | Leu | Glu 425 | Ala | His | Val | Arg | Gln 430 | Leu | Gln |
| Glu | Arg | Met 435 | Glu | Leu | Leu | Gln | Ala 440 | Glu | Gly | Ala | Thr | Ala 445 | Val | Thr | Gly |
| Val | Pro 450 | Ser | Pro | Arg | Ala | Thr 455 | Asp | Pro | Pro | Ser | His 460 | Leu | Asp | Gly | Pro |
| Pro 465 | Ala | Val | Ala | Val | Gly 470 | Gln | Cys | Pro | Leu | Val 475 | Gly | Pro | Gly | Pro | Met 480 |
| His | Arg | Arg | His | Leu 485 | Leu | Leu | Pro | Ala | Arg 490 | Val | Pro | Arg | Pro | Gly 495 | Leu |
| Ser | Glu | Ala | Leu 500 | Ser | Leu | Leu | Leu | Phe 505 | Ala | Val | Val | Leu | Ser 510 | Arg | Ala |
| Ala | Ala | Leu 515 | Gly | Cys | Ile | Gly | Leu 520 | Val | Ala | His | Ala | Gly 525 | Gln | Leu | Thr |
| Ala | Val 530 | Trp | Arg | Pro | Pro | Arg 535 | Ser | Arg | Pro | Arg | Ser 540 | Leu | Asn | Pro | Arg |
| Thr 545 | Val | Phe | Asp | Ser | Gly 550 | Ala | Pro | Leu | Glu | Asp 555 |  |  |  |  |  |

(2) INFORMATION FOR SEQ ID NO:7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Asn  Gly  Asp  Arg  Arg  Trp  Ile  Thr  Gln
    1                        5

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:8:

Leu Val Glu Asp Gly Leu Thr Ala Met Val Ser Gly
1               5                       10

( 2 ) INFORMATION FOR SEQ ID NO:9:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Phe Asp Ser Gly Ala Pro Leu Glu Asp
1               5

( 2 ) INFORMATION FOR SEQ ID NO:10:

( i ) SEQUENCE CHARACTERISTICS:
( A ) LENGTH: 11613 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| CCATGGCCTC | TCTGCACCCC | GCCTCAGGGT | CAGGGTCAGG | GTCATGCTGG | GAGCTCCCTC | 60 |
| TCCTAGGACC | CTCCCCCCAA | AAGTGGGCTC | TATGGCCCTC | TCCCTGGTT | TCCTGTGGCC | 120 |
| TGGGGCAAGC | CAGGAGGGCC | AGCATGGGGC | AGCTGCCAGG | GGCGCAGCCG | ACAGGCAGGT | 180 |
| GTTCGGCGCC | AGCCTCTCCA | GCTGCCCCAA | CAGGTGCCCA | GGCGCTGGGA | GGGCGGTGAC | 240 |
| TCACGCGGGC | CCTGTGGGAG | AACCAGCTTT | GCAGACAGGC | GCCACCAGTG | CCCCCTCCTC | 300 |
| TGCGATCCAG | GAGGGACAAC | TTTGGGTTCT | TCTGGGTGTG | TCTCCTTCTT | TTGTAGGTTC | 360 |
| TGCACCCACC | CCCACCCCCA | GCCCCAAAGT | CTCGGTTCCT | ATGAGCCGTG | TGGGTCAGCC | 420 |
| ACCATTCCCG | CCACCCCGGG | TCCCTGCGTC | CTTTAGTTCT | CCTGGCCCAG | GGCCTCCAAC | 480 |
| CTTCCAGCTG | TCCCACAAAA | CCCCTTCTTG | CAAGGGCTTT | CCAGGGCCTG | GGGCCAGGGC | 540 |
| TGGAAGGAGG | ATGCTTCCGC | TTCTGCCAGC | TGCCTTGTCT | GCCCACCTCC | TCCCCAAGCC | 600 |
| CAGGACTCGG | GCTCACTGGT | CACTGGTTTC | TTTCATTCCC | AGCACCCTGC | TCCTCTGGCC | 660 |
| CTCATATGTC | TGGCCCTCAG | TGACTGGTGT | TTGGTTTTTG | GCCTGTGTGT | AACAAACTGT | 720 |
| GTGTGACACT | TGTTTCCTGT | TTCTCCGCCT | TCCCCTGCTT | CCTCTTGTGT | CCATCTCTTT | 780 |
| CTGACCCAGG | CCTGGTTCCT | TTCCCTCCTC | CTCCCATTTC | ACAGATGGGA | AGGTGGCGGC | 840 |
| CAAGAAGGGC | CAGGCCATTC | AGCCTCTGGA | AAAACCTTCT | CCCAACCTCC | CACAGCCCCT | 900 |
| AATGACTCTC | CTGGCCTCCC | TTTAGTAGAG | GATGAAGTTG | GGTTGGCAGG | GTAAACTGAG | 960 |
| ACCGGGTGGG | GTAGGGGTCT | GGCGCTCCCG | GGAGGAGCAC | TCCTTTTGTG | GCCCGAGCTG | 1020 |
| CATCTCGCGG | CCCCTCCCCT | GCAAGGCCTG | GGGCGGGGGA | GGGGGCCAGG | GTTCCTGCTG | 1080 |
| CCTTAAAAGG | GCTCAATGTC | TTGGCTCTCT | CCTCCCTCCC | CCGTCCTCAG | CCCTGGCTGG | 1140 |
| TTCGTCCCTG | CTGGCCCACT | CTCCCGGAAC | CCCCCGGAAC | CCCTCTCTTT | CCTCCAGAAC | 1200 |
| CCACTGTCTC | CTCTCCTTCC | CTCCCCTCCC | ATACCCATCC | CTCTCTCCAT | CCTGCCTCCA | 1260 |
| CTTCTTCCAC | CCCCGGGAGT | CCAGGCCTCC | CTGTCCCCAC | AGTCCCTGAG | CCACAAGCCT | 1320 |

```
CCACCCCAGC  TGGTCCCCCA  CCCAGGCTGC  CCAGTTTAAC  ATTCCTAGTC  ATAGGACCTT  1380
GACTTCTGAG  AGGCCTGATT  GTCATCTGTA  AATAAGGGGT  AGGACTAAAG  CACTCCTCCT  1440
GGAGGACTGA  GAGATGGGCT  GGACCGGAGC  ACTTGAGTCT  GGGATATGTG  ACCATGCTAC  1500
CTTTGTCTCC  CTGTCCTGTT  CCTTCCCCCA  GCCCCAAATC  CAGGGTTTTC  CAAAGTGTGG  1560
TTCAAGAACC  ACCTGCATCT  GAATCTAGAG  GTACTGGATA  CAACCCCACG  TCTGGGCCGT  1620
TACCCAGGAC  ATTCTACATG  AGAACGTGGG  GGTGGGGCCC  TGGCTGCACC  TGAACTGTCA  1680
CCTGGAGTCA  GGGTGGAAGG  TGGAAGAACT  GGGTCTTATT  TCCTTCTCCC  CTTGTTCTTT  1740
AGGGTCTGTC  CTTCTGCAGA  CTCCGTTACC  CCACCCTAAC  CATCCTGCAC  ACCCTTGGAG  1800
CCCTCTGGGC  CAATGCCCTG  TCCCGCAAAG  GGCTTCTCAG  GCATCTCACC  TCTATGGGAG  1860
GGCATTTTTG  GCCCCCAGAA  CCTTACACGG  TGTTTATGTG  GGAAGCCCC   TGGGAAGCAG  1920
ACAGTCCTAG  GGTGAAGCTG  AGAGGCAGAG  AGAAGGGGAG  ACAGACAGAG  GGTGGGGCTT  1980
TCCCCCTTGT  CTCCAGTGCC  CTTTCTGGTG  ACCCTCGGTT  CTTTTCCCCC  ACCACCCCCC  2040
CAGCGGAGCC  CATCGTGGTG  AGGCTTAAGG  AGGTCCGACT  GCAGAGGGAC  GACTTCGAGA  2100
TTCTGAAGGT  GATCGGACGC  GGGGCGTTCA  GCGAGGTAAG  CCGAACCGGG  CGGGAGCCTG  2160
ACTTGACTCG  TGGTGGGCGG  GGCATAGGGG  TTGGGGCGGG  GCCTTAGAAA  TTGATGAATG  2220
ACCGAGCCTT  AGAACCTAGG  GCTGGGCTGG  AGGCGGGGCT  TGGGACCAAT  GGGCGTGGTG  2280
TGGCAGGTGG  GGCGGGGCCA  CGGCTGGGTG  CAGAAGCGGG  TGGAGTTGGG  TCTGGGCGAG  2340
CCCTTTTGTT  TTCCCGCCGT  CTCCACTCTG  TCTCACTATC  TCGACCTCAG  GTAGCGGTAG  2400
TGAAGATGAA  GCAGACGGGC  CAGGTGTATG  CCATGAAGAT  CATGAACAAG  TGGGACATGC  2460
TGAAGAGGGG  CGAGGTGAGG  GGCTGGGCGG  ACGTGGGGGG  CTTTGAGGAT  CCGCGCCCCG  2520
TCTCCGGCTG  CAGCTCCTCC  GGGTGCCCTG  CAGGTGTCGT  GCTTCCGTGA  GGAGAGGGAC  2580
GTGTTGGTGA  ATGGGGACCG  GCGGTGGATC  ACGCAGCTGC  ACTTCGCCTT  CCAGGATGAG  2640
AACTACCTGG  TGAGCTCCGG  GCCGGGGGGA  CTAGGAAGAG  GGACAAGAGC  CGTGCTGTC   2700
ACTGGACGAG  GAGGTGGGGA  GAGGAAGCTC  TAGGATTGGG  GGTGCTGCCC  GGAAACGTCT  2760
GTGGGAAAGT  CTGTGTGCGG  TAAGAGGGTG  TGTCAGGTGG  ATGAGGGCC   TTCCCTATCT  2820
GAGACGGGGA  TGGTGTCCTT  CACTGCCCGT  TTCTGGGGTG  ATCTGGGGA   CTCTTATAAA  2880
GATGTCTCTG  TTGCGGGGGG  TCTCTTACCT  GGAATGGGAT  AGGTCTTCAG  GAATTCTAAC  2940
GGGGCCACTG  CCTAGGGAAG  GAGTGTCTGG  GACCTATTCT  CTGGGTGTTG  GGTGGCCTCT  3000
GGGTTCTCTT  TCCCAGAACA  TCTCAGGGGG  AGTGAATCTG  CCCAGTGACA  TCCCAGGAAA  3060
GTTTTTTTGT  TTGTGTTTTT  TTTTGAGGGG  CGGGGCGGG   GCCGCAGGT   GGTCTCTGAT  3120
TTGGCCCGGC  AGATCTCTAT  GGTTATCTCT  GGGCTGGGC   TGCAGGTCTC  TGCCCAAGGA  3180
TGGGGTGTCT  CTGGGAGGGG  TTGTCCCAGC  CATCCGTGAT  GGATCAGGGC  CTCAGGGGAC  3240
TACCAACCAC  CCATGACGAA  CCCCTTCTCA  GTACCTGGTC  ATGGAGTATT  ACGTGGGCGG  3300
GGACCTGCTG  ACACTGCTGA  GCAAGTTTGG  GGAGCGGATT  CCGGCCGAGA  TGGCGCGCTT  3360
CTACCTGGCG  GAGATTGTCA  TGGCCATAGA  CTCGGTGCAC  CGGCTTGGCT  ACGTGCACAG  3420
GTGGGCGCAG  CATGGCCGAG  GGGATAGCAA  GCTTGTTCCC  TGGCCGGGTT  CTTGGAAGGT  3480
CAGAGCCCAG  AGAGGCCAGG  GCCTGGAGAG  GGACCTTCTT  GGTTGGGGCC  CACCGGGGGG  3540
TGCCTGGGAG  TAGGGGTCAG  AACTGTAGAA  GCCCTACAGG  GGCGGAACCC  GAGGAAGTGG  3600
GGTCCAGGT   GGCACTGCCC  GGAGGGGCGG  AGCCTGGTGG  GACCACAGAA  GGGAGGTTCA  3660
TTTATCCCAC  CCTTCTCTTT  TCCTCCGTGC  AGGGACATCA  AACCCGACAA  CATCCTGCTG  3720
```

```
GACCGCTGTG GCCACATCCG CCTGGCCGAC TTCGGCTCTT GCCTCAAGCT GCGGGCAGAT   3780
GGAACGGTGA GCCAGTGCCC TGGCCACAGA GCAACTGGGG CTGCTGATGA GGGATGGAAG   3840
GCACAGAGTG TGGGAGCGGG ACTGGATTTG GAGGGGAAAA GAGGTGGTGT GACCCAGGCT   3900
TAAGTGTGCA TCTGTGTGGC GGAGTATTAG ACCAGGCAGA GGGAGGGGCT AAGCATTTGG   3960
GGAGTGGTTG GAAGGAGGGC CCAGAGCTGG TGGGCCCAGA GGGGTGGGCC CAAGCCTCGC   4020
TCTGCTCCTT TTGGTCCAGG TGCGGTCGCT GGTGGCTGTG GGCACCCAG ACTACCTGTC    4080
CCCCGAGATC CTGCAGGCTG TGGGCGGTGG GCCTGGGACA GGCAGCTACG GCCCGAGTG    4140
TGACTGGTGG GCGCTGGGTG TATTCGCCTA TGAAATGTTC TATGGGCAGA CGCCCTTCTA   4200
CGCGGATTCC ACGGCGGAGA CCTATGGCAA GATCGTCCAC TACAAGGTGA GCACGGCCGC   4260
AGGGAGACCT GGCCTCTCCC GGTAGGCGCT CCCAGCTATC GCCTCCTCTC CCTCTGAGCA   4320
GGAGCACCTC TCTCTGCCGC TGGTGGACGA AGGGGTCCCT GAGGAGGCTC GAGACTTCAT   4380
TCAGCGGTTG CTGTGTCCCC GGAGACACG GCTGGGCCGG GGTGGAGCAG GCGACTTCCG     4440
GACACATCCC TTCTTCTTTG GCCTCGACTG GGATGGTCTC CGGGACAGCG TGCCCCCCTT   4500
TACACCGGAT TTCGAAGGTG CCACCGACAC ATGCAACTTC GACTTGGTGG AGGACGGGCT   4560
CACTGCCATG GTGAGCGGGG GCGGGGTAGG TACCTGTGGC CCCTGCTCGG CTGCGGGAAC   4620
CTCCCCATGC TCCCTCCATA AAGTTGGAGT AAGGACAGTG CCTACCTTCT GGGGTCCTGA   4680
ATCACTCATT CCCCAGAGCA CCTGCTCTGT GCCCATCTAC TACTGAGGAC CCAGCAGTGA   4740
CCTAGACTTA CAGTCCAGTG GGGAACACA GAGCAGTCTT CAGACAGTAA GGCCCCAGAG    4800
TGATCAGGGC TGAGACAATG GAGTGCAGGG GGTGGGGGAC TCCTGACTCA GCAAGGAAGG   4860
TCCTGGAGGG CTTTCTGGAG TGGGGAGCTA TCTGAGCTGA GACTTGGAGG GATGAGAAGC   4920
AGGAGAGGAC TCCTCCTCCC TTAGGCCGTC TCTCTTCACC GTGTAACAAG CTGTCATGGC   4980
ATGCTTGCTC GGCTCTGGGT GCCCTTTTGC TGAACAATAC TGGGGATCCA GCACGGACCA   5040
GATGAGCTCT GGTCCCTGCC CTCATCCAGT TGCAGTCTAG AGAATTAGAG AATTATGGAG   5100
AGTGTGGCAG GTGCCCTGAA GGGAAGCAAC AGGATACAAG AAAAAATGAT GGGGCCAGGC   5160
ACGGTGCTCA CGCCTGTAAC CCCAGCAATT TGGCAGGCCG AAGTGGGTGG ATTGCTTGAG   5220
CCCAGGAGTT CGAGACCAGC CTGGGCAATG TGGTGAGACC CCCGTCTCTA CAAAAATGTT   5280
TTAAAAATTG GTTGGGCGTG GTGGCGCATG CCTGTATACT CAGCTACTAG GGTGGCCGAC   5340
GTGGGCTTGA GCCCAGGAGG TCAAGGCTGC AGTGAGCTGT GATTGTGCCA CTGCACTCCA   5400
GCCTGGGCAA CGGAGAGAGA CTCTGTCTCA AAAATAAGAT AAACTGAAAT TAAAAAATAG   5460
GCTGGGCTGG CCGGGCGTGG TGGCTCACGC CTGTAATCTC AGCACTTTGG GAGGCCGAGG   5520
CGGGTGGATC ACGAGGTCAG AAGATGGAGA CCAGCCTGGC CAGCGTGGCG AAACCCCGTC   5580
TCTACCAAAA ATATAAAAAA TTAGCCAGGC GTGGTAGAGG GCGCCTGTAA TCTCAGCTAC   5640
TCAGGACGCT GAGGCAGGAG AATCGCCTGA ACCTGGGAGG CGGAGGTTGC AGTGAGCTGA   5700
GATTGCACCA CTGCACTCCA GCCTGGGTAA CAGAGCGAGA CTCCGTATCA AAGAAAAGA    5760
AAAAGAAAA AATGCTGGAG GGGCCACTTT AGATAAGCCC TGAGTTGGGG CTGGTTTGGG    5820
GGGAACATGT AAGCCAAGAT CAAAAGCAG TGAGGGGCCC GCCCTGACGA CTGCTGCTCA    5880
CATCTGTGTG TCTTGCGCAG GAGACACTGT CGGACATTCG GGAAGGTGCG CCGCTAGGGG   5940
TCCACCTGCC TTTTGTGGGC TACTCCTACT CCTGCATGGC CCTCAGGTAA GCACTGCCCT   6000
GGACGGCCTC CAGGGGCCAC GAGGCTGCTT GAGCTTCCTG GGTCCTGCTC CTTGGCAGCC   6060
AATGGAGTTG CAGGATCAGT CTTGGAACCT TACTGTTTTG GGCCCAAAGA CTCCTAAGAG   6120
```

```
GCCAGAGTTG GAGGACCTTA AATTTTCAGA TCTATGTACT TCAAAATGTT AGATTGAATT    6180
TTAAAACCTC AGAGTCACAG ACTGGGCTTC CCAGAATCTT GTAACCATTA ACTTTTACGT    6240
CTGTAGTACA CAGAGCCACA GGACTTCAGA ACTTGGAAAA TATGAAGTTT AGACTTTTAC    6300
AATCAGTTGT AAAAGAATGC AAATTCTTTG AATCAGCCAT ATAACAATAA GGCCATTTAA    6360
AAGTATTAAT TTAGGCGGGC CGCGGTGGCT CACGCCTGTA ATCCTAGCAC TTTGGGAGGC    6420
CAAGGCAGGT GGATCATGAG GTCAGGAGAT CGAGACCATC CTGGCTAACA CGGTGAAACC    6480
CCGTCTCTAC TAAAAATACA AAAAATTAG CCGGGCATGG TGGCGGGCGC TTGCGGTCCC     6540
AGCTACTTGG GAGGCGAGGC AGGAGAATGG CATGAACCCG GAGGCGGAG CTTGCAGTGA     6600
GCCGAGATCA TGCCACTGCA CTCCAGCCTG GCGACAGAG CAAGACTCCG TCTCAAAAAA     6660
AAAAAAAAA AAAGTATTTA TTTAGGCCGG GTGTGGTGGC TCACGCCTGT AATTCCAGTG     6720
CTTTGGGAGG ATGAGGTGGG TGGATCACCT GAGGTCAGGA GTTCGAGACC AGCCTGACCA    6780
ACGTGGAGAA ACCTCATCTC TACTAAAAAA CAAAATTAGC CAGGCATGGT GGCATATACC    6840
TGTAATCCCA GCTACTCAGG AGGCTGAGGC AGGAGAATCA GAACCCAGGA GGGGAGGTT    6900
GTGGTTAGCT GAGATCGTGC CATTGCATTC CAGCCTGGGC AACAAGAGTG AAACTTCATC    6960
TCAAAAAAAA AAAAAAAAA GTACTAATTT ACAGGCTGGG CATGGTGGCT CACGCTTGGA    7020
ATCCCAGCAC TTTGGGAGGC TGAAGTGGAC GGATTGCTTC AGCCCAGGAG TTCAAGACCA    7080
GCCTGAGCAA CATAATGAGA CCCTGTCTCT ACAAAAATT GAAAAATCG TGCCAGGCAT     7140
GGTGGTCTGT GCCTGCAGTC CTAGCTACTC AGGAGTCTGA AGTAGGAGAA TCACTTGAGC    7200
CTGGAGTTTG AGGCTTCAGT GAGCCATGAT AGATTCCAGC CTAGGCAACA AGTGAGACC    7260
TGGTCTCAAC AAAAGTATTA ATTACACAAA TAATGCATTG CTTATCACAA GTAAATTAGA    7320
AAATACAGAT AAGGAAAAGG AAGTTGATAT CTCGTGAGCT CACCAGATGG CAGTGGTCCC    7380
TGGCTCACAC GTGTACTGAC ACATGTTTAA ATAGTGGAGA ACAGGTGTTT TTTTGGTTTG    7440
TTTTTTTCCC CTTCCTCATG CTACTTTGTC TAAGAGAACA GTTGGTTTTC TAGTCAGCTT    7500
TTATTACTGG ACAACATTAC ACATACTATA CCTTATCATT AATGAACTCC AGCTTGATTC    7560
TGAACCGCTG CGGGGCCTGA ACGGTGGGTC AGGATTGAAC CCATCCTCTA TTAGAACCCA    7620
GGCGCATGTC CAGGATAGCT AGGTCCTGAG CCGTGTTCCC ACAGGAGGGA CTGCTGGGTT    7680
GGAGGGGACA GCCACTTCAT ACCCAGGGA GGAGCTGTCC CCTTCCCACA GCTGAGTGGG     7740
GTGTGCTGAC CTCAAGTTGC CATCTTGGGG TCCCATGCCC AGTCTTAGGA CCACATCTGT    7800
GGAGGTGGCC AGAGCCAAGC AGTCTCCCCA TCAGGTCGGC CTCCCTGTCC TGAGGCCCTG    7860
AGAAGAGGGG TCTGCAGCGG TCACATGTCA AGGGAGGAGA TGAGCTGACC CTAGAACATG    7920
GGGGTCTGGA CCCCAAGTCC CTGCAGAAGG TTTAGAAAGA GCAGCTCCCA GGGCCCAAG     7980
GCCAGGAGAG GGGCAGGGCT TTTCCTAAGC AGAGGAGGGG CTATTGGCCT ACCTGGGACT    8040
CTGTTCTCTT CGCTCTGCTG CTCCCCTTCC TCAAATCAGG AGGTCTTGGA AGCAGCTGCC    8100
CCTACCCACA GGCCAGAAGT TCTGGTTCTC CACCAGATAA TCAGCATTCT GTCTCCCTCC    8160
CCACTCCCTC CTCCTCTCCC CAGGGACAGT GAGGTCCCAG GCCCACACC CATGGAAGTG     8220
GAGGCCGAGC AGCTGCTTGA GCCACACGTG CAAGCGCCCA GCCTGGAGCC CTCGGTGTCC    8280
CCACAGGATG AAACAGTAAG TTGGTGGAGG GGAGGGGGTC CGTCAGGGAC AATTGGGAGA    8340
GAAAGGTGA GGGCTTCCCG GGTGGCGTGC ACTGTAGAGC CCTCTAGGGA CTTCCTGAAC     8400
AGAAGCAGAC AGAAACCACG GAGAGACGAG GTTACTTCAG ACATGGGACG GTCTCTGTAG    8460
TTACAGTGGG GCATTAAGTA AGGGTGTGTG TGTTGCTGGG GATCTGAGAA GTCGATCTTT    8520
```

```
GAGCTGAGCG  CTGGTGAAGG  AGAAACAAGC  CATGGAAGGA  AAGGTGCCAA  GTGGTCAGGC   8580
GAGAGCCTCC  AGGGCAAAGG  CCTTGGGCAG  GTGGGAATCC  TGATTTGTTC  CTGAAAGGTA   8640
GTTTGGCTGA  ATCATTCCTG  AGAAGGCTGG  AGAGGCCAGC  AGGAAACAAA  ACCCAGCAAG   8700
GCCTTTTGTC  GTGAGGGCAT  TAGGGAGCTG  GAGGGATTTT  GAGCAGCAGA  GGGACATAGG   8760
TTGTGTTAGT  GTTTGAGCAC  CAGCCCTCTG  GTCCCTGTGT  AGATTTAGAG  GACCAGACTC   8820
AGGGATGGGG  CTGAGGGAGG  TAGGGAAGGG  AGGGGGCTTG  GATCATTGCA  GGAGCTATGG   8880
GGATTCCAGA  AATGTTGAGG  GGACGGAGGA  GTAGGGATA   AACAAGGATT  CCTAGCCTGG   8940
AACCAGTGCC  CAAGTCCTGA  GTCTTCCAGG  AGCCACAGGC  AGCCTTAAGC  CTGGTCCCCA   9000
TACACAGGCT  GAAGTGGCAG  TTCCAGCGGC  TGTCCCTGCG  GCAGAGGCTG  AGGCCGAGGT   9060
GACGCTGCGG  GAGCTCCAGG  AAGCCCTGGA  GGAGGAGGTG  CTCACCCGGC  AGAGCCTGAG   9120
CCGGGAGATG  GAGGCCATCC  GCACGGACAA  CCAGAACTTC  GCCAGGTCGG  ATCGGGGCC   9180
GGGGCCGGGG  CCGGGATGCG  GGCCGGTGGC  AACCCTTGGC  AGCCCCTCTC  GTCCGGCCCG   9240
GACGGACTCA  CCGTCCTTAC  CTCCCCACAG  TCAACTACGC  GAGGCAGAGG  CTCGGAACCG   9300
GGACCTAGAG  GCACACGTCC  GGCAGTTGCA  GGAGCGGATG  GAGTTGCTGC  AGGCAGAGGG   9360
AGCCACAGGT  GAGTCCCTCA  TGTGTCCCCT  TCCCCGGAGG  ACCGGGAGGA  GGTGGGCCGT   9420
CTGCTCCGCG  GGGCGTGTAT  AGACACCTGG  AGGAGGGAAG  GGACCCACGC  TGGGGCACGC   9480
CGCGCCACCG  CCCTCCTTCG  CCCCTCCACG  CGCCCTATGC  CTCTTTCTTC  TCCTTCCAGC   9540
TGTCACGGGG  GTCCCCAGTC  CCCGGGCCAC  GGATCCACCT  TCCCATGTAA  GACCCCTCTC   9600
TTTCCCCTGC  CTCAGACCTG  CTGCCCATTC  TGCAGATCCC  CTCCCTGGCT  CCTGGTCTCC   9660
CCGTCCAGAT  ATAGGGCTCA  CCCTACGTCT  TTGCGACTTT  AGAGGGCAGA  AGCCCTTTAT   9720
TCAGCCCCAG  ATCTCCCTCC  GTTCAGGCCT  CACCAGATTC  CCTCCGGGAT  CTCCCTAGAT   9780
AACCTCCCCA  ACCTCGATTC  CGCTCGCTGT  CTCTCGCCCC  ACCGCTGAGG  GCTGGGCTGG   9840
GCTCCGATCG  GGTCACCTGT  CCCTTCTCTC  TCCAGCTAGA  TGGCCCCCCG  GCCGTGGCTG   9900
TGGGCCAGTG  CCCGCTGGTG  GGGCCAGGCC  CCATGCACCG  CCGCCACCTG  CTGCTCCCTG   9960
CCAGGGTACG  TCCGGCTGCC  CACGCCCCCC  TCCGCCGTCG  CGCCCCGCGC  TCCACCCGCC  10020
CCGTGCCACC  CGCTTAGCTG  CGCATTTGCG  GGGCTGGGCC  CACGGCAGGA  GGGCGGATCT  10080
TCGGGCAGCC  AATCAACACA  GGCCGCTAGG  AAGCAGCCAA  TGACGAGTTC  GGACGGGATT  10140
CGAGGCGTGC  GAGTGGACTA  ACAACAGCTG  TAGGCTGTTG  GGGCGGGGGC  GGGGCGCAGG  10200
GAAGAGTGCG  GGCCCACCTA  TGGGCGTAGG  CGGGGCGAGT  CCCAGGAGCC  AATCAGAGGC  10260
CCATGCCGGG  TGTTGACCTC  GCCCTCTCCC  CGCAGGTCCC  TAGGCCTGGC  CTATCGGAGG  10320
CGCTTTCCCT  GCTCCTGTTC  GCCGTTGTTC  TGTCTCGTGC  CGCCGCCCTG  GCTGCATTG   10380
GGTTGGTGGC  CCACGCCGGC  CAACTCACCG  CAGTCTGGCG  CCGCCCAGGA  GCCGCCCGCG  10440
CTCCCTGAAC  CCTAGAACTG  TCTTCGACTC  CGGGGCCCCG  TTGGAAGACT  GAGTGCCCGG  10500
GGCACGGCAC  AGAAGCCGCG  CCCACCGCCT  GCCAGTTCAC  AACCGCTCCG  AGCGTGGGTC  10560
TCCGCCCAGC  TCCAGTCCTG  TGATCCGGGC  CCGCCCCCTA  GCGGCCGGGG  AGGGAGGGGC  10620
CGGGTCCGCG  GCCGGCGAAC  GGGGCTCGAA  GGGTCCTTGT  AGCCGGGAAT  GCTGCTGCTG  10680
CTGCTGCTGC  TGCTGCTGCT  GCTGGGGGGA  TCACAGACCA  TTTCTTTCTT  TCGGCCAGGC  10740
TGAGGCCCTG  ACGTGGATGG  GCAAACTGCA  GGCCTGGGAA  GGCAGCAAGC  CGGGCCGTCC  10800
GTGTTCCATC  CTCCACGCAC  CCCCACCTAT  CGTTGGTTCG  CAAAGTGCAA  AGCTTTCTTG  10860
TGCATGACGC  CCTGCTCTGG  GGAGCGTCTG  GCGCGATCTC  TGCCTGCTTA  CTCGGGAAAT  10920
```

| | | | | | |
|---|---|---|---|---|---|
| TTGCTTTTGC | CAAACCCGCT | TTTTCGGGGA | TCCCGCGCCC | CCCTCCTCAC | TTGCGCTGCT | 10980
| CTCGGAGCCC | CAGCCGGCTC | CGCCCGCTTC | GGCGGTTTGG | ATATTTATTG | ACCTCGTCCT | 11040
| CCGACTCGCT | GACAGGCTAC | AGGACCCCCA | ACAACCCCAA | TCCACGTTTT | GGATGCACTG | 11100
| AGACCCCGAC | ATTCCTCGGT | ATTTATTGTC | TGTCCCCACC | TAGGACCCCC | ACCCCCGACC | 11160
| CTCGCGAATA | AAAGGCCCTC | CATCTGCCCA | AAGCTCTGGA | CTCCACAGTG | TCCGCGGTTT | 11220
| GCGTTGTGGG | CCGGAGCTCC | GCAGCGGGCC | AATCCGGAGG | CGTGTGGAGG | CGGCCGAAGG | 11280
| TCTGGGAGGA | GCTAGCGGGA | TGCGAAGCGG | CCGAATCAGG | GTTGGGGGAG | GAAAAGCCAC | 11340
| GGGGCGGGGC | TTTGGCGTCC | GGCCAATAGG | AGGGCGAGCG | GGCCACCCGG | AGGCACCGCC | 11400
| CCCGCCCAGC | TGTGGCCCAG | CTGTGCCACC | GAGCGTCGAG | AAGAGGGGGC | TGGGCTGGCA | 11460
| GCGCGCGCGG | CCATCCTCCT | TCCACTGCGC | CTGCGCACGC | CACGCGCATC | CGCTCCTGGG | 11520
| ACGCAAGCTC | GAGAAAAGTT | GCTGCAAACT | TTCTAGCCCG | TTCCCCGCCC | CTCCTCCCGG | 11580
| CCAGACCCGC | CCCCCCTGCG | GAGCCGGGAA | TTC | | | 11613

( 2 ) INFORMATION FOR SEQ ID NO:11:

( i ) SEQUENCE CHARACTERISTICS:
        ( A ) LENGTH: 3182 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| GCCACAAGCC | TCCACCCCAG | CTGGTCCCCC | ACCCAGGCTG | CCCAGTTTAA | CATTCCTAGT | 60
| CATAGGACCT | TGACTTCTGA | GAGGCCTGAT | TGTCATCTGT | AAATAAGGGG | TAGGACTAAA | 120
| GCACTCCTCC | TGGAGGACTG | AGAGATGGGC | TGGACCGGAG | CACTTGAGTC | TGGGATATGT | 180
| GACCATGCTA | CCTTTGTCTC | CCTGTCCTGT | TCCTTCCCCC | AGCCCCAAAT | CCAGGGTTTT | 240
| CCAAAGTGTG | GTTCAAGAAC | CACCTGCATC | TGAATCTAGA | GGTACTGGAT | ACAACCCCAC | 300
| GTCTGGGCCG | TTACCCAGGA | CATTCTACAT | GAGAACGTGG | GGGTGGGGCC | CTGGCTGCAC | 360
| CTTGAACTGT | CACCTGGAGT | CAGGGTGGAA | GGTGGAAGAA | CTGGGTCTTA | TTTCCTTCTC | 420
| CCCTTGTTCT | TTAGGGTCTG | TCCTTCTGCA | GACTCCGTTA | CCCCACCCTA | ACCATCCTGC | 480
| ACACCCTTGG | AGCCCTCTGG | GCCAATGCCC | TGTCCCGCAA | AGGGCTTCTC | AGGCATCTCA | 540
| CCTCTATGGG | AGGGCATTTT | TGGCCCCCAG | AACCTTACAC | GGTGTTTATG | TGGGGAAGCC | 600
| CCTGGGAAGC | AGACAGTCCT | AGGGTGAAGC | TGAGAGGCAG | AGAGAAGGGG | AGACAGACAG | 660
| AGGGTGGGGC | TTTCCCCCTT | GTCTCCAGTG | CCCTTTCTGG | TGACCCTCGG | TTCTTTTCCC | 720
| CCACCACCCC | CCCAGCGGAG | CCCATCGTGG | TGAGGCTTAA | GGAGGTCCGA | CTGCAGAGGG | 780
| ACGACTTCGA | GATTCTGAAG | GTGATCGGAC | GCGGGGCGTT | CAGCGAGGTA | GCGGTAGTGA | 840
| AGATGAAGCA | GACGGGCCAG | GTGTATGCCA | TGAAGATCAT | GAACAAGTGG | GACATGCTGA | 900
| AGAGGGGCGA | GGTGTCGTGC | TTCCGTGAGG | AGAGGGACGT | GTTGGTGAAT | GGGGACCGGC | 960
| GGTGGATCAC | GCAGCTGCAC | TTCGCCTTCC | AGGATGAGAA | CTACCTGTAC | CTGGTCATGG | 1020
| AGTATTACGT | GGGCGGGGAC | CTGCTGACAC | TGCTGAGCAA | GTTTGGGGAG | CGGATTCCGG | 1080
| CCGAGATGGC | GCGCTTCTAC | CTGGCGGAGA | TTGTCATGGC | CATAGACTCG | GTGCACCGGC | 1140
| TTGGCTACGT | GCACAGGGAC | ATCAAACCCG | ACAACATCCT | GCTGGACCGC | TGTGGCCACA | 1200
| TCCGCCTGGC | CGACTTCGGC | TCTTGCCTCA | AGCTGCGGGC | AGATGGAACG | GTGCGGTCGC | 1260

-continued

```
TGGTGGCTGT GGGCACCCCA GACTACCTGT CCCCCGAGAT CCTGCAGGCT GTGGGCGGTG    1320
GGCCTGGGAC AGGCAGCTAC GGGCCCGAGT GTGACTGGTG GGCGCTGGGT GTATTCGCCT    1380
ATGAAATGTT CTATGGGCAG ACGCCTTCT  ACGCGGATTC CACGGCGGAG ACCTATGGCA    1440
AGATCGTCCA CTACAAGGAG CACCTCTCTC TGCCGCTGGT GGACGAAGGG GTCCCTGAGG    1500
AGGCTCGAGA CTTCATTCAG CGGTTGCTGT GTCCCCCGGA GACACGGCTG GCCGGGGTG     1560
GAGCAGGCGA CTTCCGGACA CATCCCTTCT TCTTTGGCCT CGACTGGGAT GGTCTCCGGG    1620
ACAGCGTGCC CCCCTTTACA CCGGATTTCG AAGGTGCCAC CGACACATGC AACTTCGACT    1680
TGGTGGAGGA CGGGCTCACT GCCATGGTGA GCGGGGGCGG GGAGACACTG TCGGACATTC    1740
GGGAAGGTGC GCCGCTAGGG GTCCACCTGC CTTTTGTGGG CTACTCCTAC TCCTGCATGG    1800
CCCTCAGGGA CAGTGAGGTC CCAGGCCCCA CACCCATGGA ACTGGAGGCC GAGCAGCTGC    1860
TTGAGCCACA CGTGCAAGCG CCCAGCCTGG AGCCCTCGGT GTCCCCACAG GATGAAACAG    1920
CTGAAGTGGC AGTTCCAGCG GCTGTCCCTG CGGCAGAGGC TGAGGCCGAG GTGACGCTGC    1980
GGGAGCTCCA GGAAGCCCTG GAGGAGGAGG TGCTCACCCG GCAGAGCCTG AGCCGGGAGA    2040
TGGAGGCCAT CCGCACGGAC AACCAGAACT TCGCCAGTCA ACTACGCGAG GCAGAGGCTC    2100
GGAACCGGGA CCTAGAGGCA CACGTCCGGC AGTTGCAGGA GCGGATGGAG TTGCTGCAGG    2160
CAGAGGGAGC CACAGCTGTC ACGGGGGTCC CCAGTCCCCG GGCCACGGAT CCACCTTCCC    2220
ATCTAGATGG CCCCCCGGCC GTGGCTGTGG GCCAGTGCCC GCTGGTGGGG CCAGGCCCCA    2280
TGCACCGCCG CCACCTGCTG CTCCCTGCCA GGGTCCCTAG GCCTGGCCTA TCGGAGGCGC    2340
TTTCCCTGCT CCTGTTCGCC GTTGTTCTGT CTCGTGCCGC CGCCCTGGGC TGCATTGGGT    2400
TGGTGGCCCA CGCCGGCCAA CTCACCGCAG TCTGGCGCCC GCCCAGGAGC CGCCCGCGCT    2460
CCCTGAACCC TAGAACTGTC TTCGACTCCG GGCCCCGTT  GGAAGACTGA GTGCCCGGGG    2520
CACGGCACAG AAGCCGCGCC CACCGCCTGC CAGTTCACAA CCGCTCCGAG CGTGGGTCTC    2580
CGCCCAGCTC CAGTCCTGTG ACCGGGCCCG CCCCTAGCG  GCCGGGGAGG GAGGGGCCGG    2640
GTCCGCGGCC GGCGAACGGG GCTCGAAGGG TCCTTGTAGC CGGGAATGCT GCTGCTGCTG    2700
CTGGGGGGAT CACAGACCAT TTCTTTCTTT CGGCCAGGCT GAGGCCCTGA CGTGGATGGG    2760
CAAACTGCAG GCCTGGGAAG GCAGCAAGCC GGGCCGTCCG TGTTCCATCC TCCACGCACC    2820
CCCACCTATC GTTGGTTCGC AAAGTGCAAA GCTTTCTTGT GCATGACGCC CTGCTCTGGG    2880
GAGCGTCTGG CGCGATCTCT GCCTGCTTAC TCGGGAAATT TGCTTTTGCC AAACCCGCTT    2940
TTTCGGGGAT CCCGCGCCCC CCTCCTACTT GCGCTGCTCT CGGAGCCCCA GCCGCTCCGC    3000
CCGCTTCGGC GGTTTGGATA TTTATTGACC TCGTCCTCCG ACTCGCTGAC AGGCTACAGG    3060
ACCCCCAACA ACCCCAATCC ACGTTTTGGA TGCACTGAGA CCCCGACATT CCTCGGTATT    3120
TATTGTCTGT CCCCACCTAG GACCCCACC  CCCGACCCTC GCGAATAAAA GGCCCTCCAT    3180
CG                                                                  3182
```

( 2 ) INFORMATION FOR SEQ ID NO:12:

( i ) SEQUENCE CHARACTERISTICS:
            ( A ) LENGTH: 24 base pairs
            ( B ) TYPE: nucleic acid
            ( C ) STRANDEDNESS: double
            ( D ) TOPOLOGY: linear ( i i ) MOLECULE TYPE: DNA (genomic)

( x i ) SEQUENCE DESCRIPTION: SEQ ID NO:12:

```
CACCTCTCTC TGCCGCTGGT GGAC                                            24
```

( 2 ) INFORMATION FOR SEQ ID NO:13:

( i ) SEQUENCE CHARACTERISTICS:
      ( A ) LENGTH: 24 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:13:

CCTAGCGGCG CACCTTCCCG AATG    24